(12) United States Patent
Protopopova et al.

(10) Patent No.: US 7,652,039 B2
(45) Date of Patent: Jan. 26, 2010

(54) METHODS OF USE AND COMPOSITIONS FOR THE DIAGNOSIS AND TREATMENT OF INFECTIOUS DISEASE

(75) Inventors: Marina Nikolaevna Protopopova, Silver Spring, MD (US); Elena Bogatcheva, Bethesda, MD (US)

(73) Assignee: Sequella, Inc., Rockville, MD (US)

( * ) Notice: Subject to any disclaimer, the term of this patent is extended or adjusted under 35 U.S.C. 154(b) by 729 days.

(21) Appl. No.: 10/441,272

(22) Filed: May 19, 2003

(65) Prior Publication Data

US 2004/0024022 A1    Feb. 5, 2004

Related U.S. Application Data

(60) Provisional application No. 60/381,244, filed on May 17, 2002.

(51) Int. Cl.
*A61K 31/445* (2006.01)
*A61K 31/40* (2006.01)
*A61K 31/04* (2006.01)
*A61K 31/13* (2006.01)

(52) U.S. Cl. ............... 514/317; 514/408; 514/326; 514/667; 514/659

(58) Field of Classification Search ......... 514/315–327, 514/408, 667, 659
See application file for complete search history.

(56) References Cited

U.S. PATENT DOCUMENTS

| | | | |
|---|---|---|---|
| 2,623,878 | A | 12/1952 | Isler et al. |
| 2,709,169 | A | 5/1955 | Morren et al. |
| 3,176,040 | A | 3/1965 | Wilkinson et al. |
| 3,197,468 | A | 7/1965 | Sensi et al. |
| 3,553,257 | A | 1/1971 | Halmos et al. |
| 3,579,586 | A | 5/1971 | Zoja |
| 3,579,587 | A | 5/1971 | Zoja |
| 3,718,655 | A | 2/1973 | Ferrer-Salat et al. |
| 3,769,347 | A | 10/1973 | Kazan |
| 3,829,493 | A | 8/1974 | Butula et al. |
| 3,847,991 | A | 11/1974 | Bernardi et al. |
| 3,855,300 | A | 12/1974 | Takahashi et al. |
| 3,876,702 | A | 4/1975 | Petersen et al. |
| 3,878,201 | A | 4/1975 | Tomcufcik |
| 3,931,152 | A | 1/1976 | Tomcufcik et al. |
| 3,931,157 | A | 1/1976 | Child et al. |
| 3,944,608 | A | 3/1976 | Singh |
| 3,944,616 | A | 3/1976 | Kazan |
| 3,944,617 | A | 3/1976 | Singh |
| 3,944,618 | A | 3/1976 | Singh |
| 3,944,619 | A | 3/1976 | Singh |
| 3,953,513 | A | 4/1976 | Oppici |
| 3,979,457 | A | 9/1976 | Fujii et al. |
| 4,006,234 | A | 2/1977 | Child et al. |
| RE29,358 | E | 8/1977 | Tomcufcik |
| RE29,588 | E | 3/1978 | Halmos et al. |
| 4,150,030 | A | 4/1979 | Singh |
| 4,262,122 | A | 4/1981 | Lees et al. |
| 4,450,274 | A | 5/1984 | Park |
| 5,104,875 | A | 4/1992 | Jürgen et al. |
| 5,439,891 | A | 8/1995 | Kapil et al. |
| 5,864,045 | A | 1/1999 | Burholder et al. |
| 5,922,282 | A | 7/1999 | Ledley |
| 5,985,935 | A | 11/1999 | Kharazmi et al. |
| 7,456,222 | B2 | 11/2008 | Protopopova et al. |

FOREIGN PATENT DOCUMENTS

| | | |
|---|---|---|
| FR | 2007524 | 4/1969 |
| GB | 729332 | 5/1955 |
| GB | 961317 | 6/1964 |
| GB | 1234349 | 6/1971 |
| RU | 2168986 | 6/2001 |
| WO | WO 99/51213 A2 | 10/1999 |

OTHER PUBLICATIONS

Arain, T.M., et al., "Bioluminescence Screening In Vitro (Bio-Siv) Assays for High-Volume Antimycobacterial Drug Discovery," Antimicrob. Agents Chemother., 1996, vol. 40, No. 6, pp. 1536-1541.
Barry, C.E., III, et al., "Use of Genomics and Combinatorial Chemistry in the Development of New Antimycobacterial Drugs," Biochem. Pharmacol., 2000, vol. 59, pp. 221-231.
Bass, J.B., Jr., et al., "Treatment of Tuberculosis and Tuberculosis Infection in Adults and Children," Am. J. Respir. Crit. Care Med., 1994, vol. 149, pp. 1359-1374.
Belanger, A.E., et al., "The EmbAB Genes of *Mycobacterium avium* Encode An Arabinosyl Transferase Involved in Cell Wall Arabinan Biosynthesis that is the Target for the Antimycobacterial Drug Ethambutol," Proc. Natl. Acad. Sci., 1996, vol. 93, pp. 11919-11924.
Brown, D.S., et al., "Merrifield, Alpha-MethoxyPhenyl (MAMP) Resin; A New Versatile Solid Support for the Synthesis of Secondary Amides," Tetrahedron Lett., 1998, vol. 39, pp. 8533-8536.
Chan-Tack, K.M., "Antituberculosis-Drug Resistance," correspondence in N. Engl. J. Med., 1998, vol. 339, No. 15, p. 1079.
Cole, S.T., at al., "Deciphering the Biology of *Mycobacterium tuberculosis* from the Complete Genome Sequence," Nature, 1998, vol. 393, pp. 537-544, [Erratum, Nature, 1998, vol. 396, p. 190].
Cuervo, J.H., et al., "Polyalkylamine Chemical Combinatorial Libraries," in Peptides 1994: Proceedings of the European Peptide Symposium, Maia HSL Ed., Esom: Leiden, 1995, pp. 465-466.
Cynamon, et al., "Activities of Several Novel Oxazolidinones Against *Mycobacterium tuberculosis* in a Murine Model," 1999, vol. 43, No. 5, pp. 1189-1191.

(Continued)

*Primary Examiner*—Ardin Marschel
*Assistant Examiner*—Donna Jagoe
(74) *Attorney, Agent, or Firm*—King & Spalding

(57) ABSTRACT

Methods and compositions for treating disease caused by infectious agents, particularly tuberculosis. In particular, methods and compositions comprising substituted diamines for the treatment of infectious diseases are provided. In one embodiment, these methods and compositions are used for the treatment of mycobacterial infections, including, but not limited to, tuberculosis.

16 Claims, 26 Drawing Sheets

OTHER PUBLICATIONS

Figure 1:
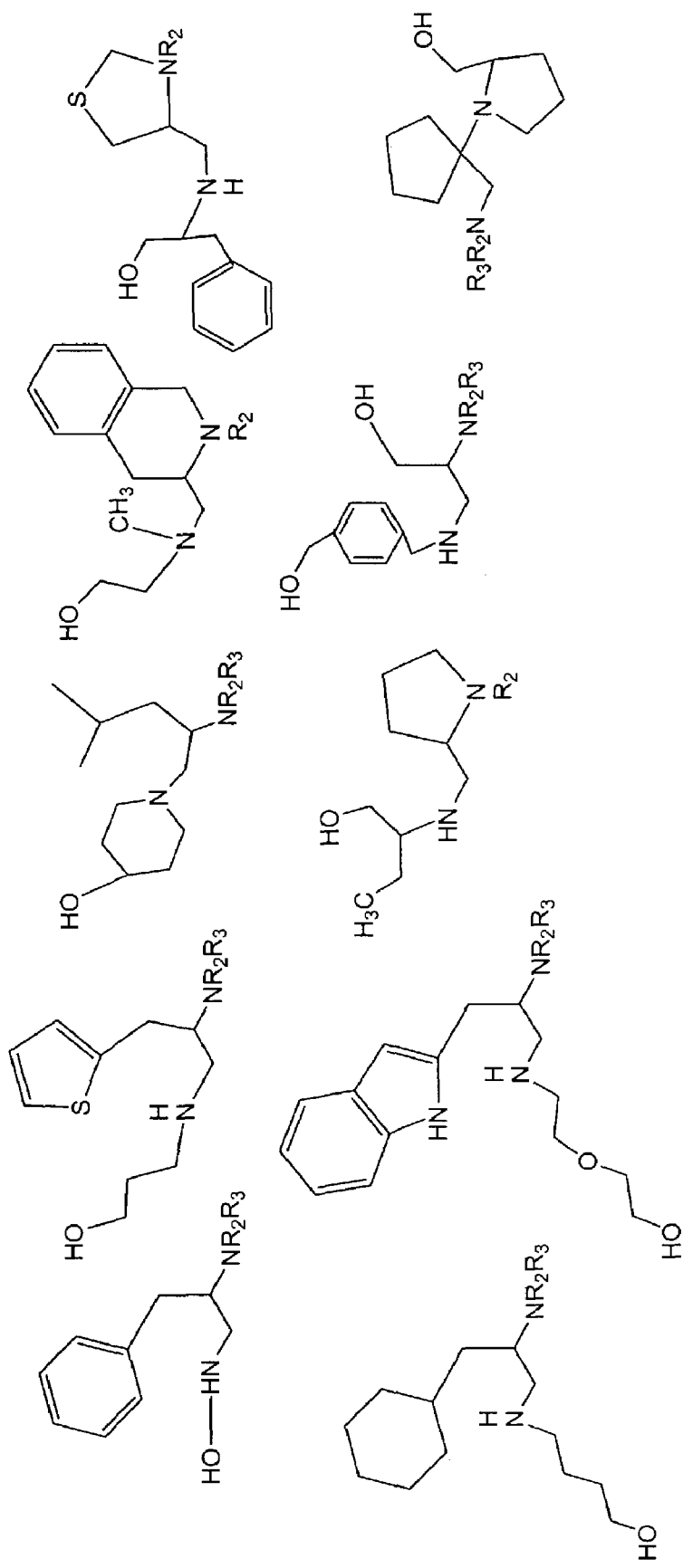
Figure 2:
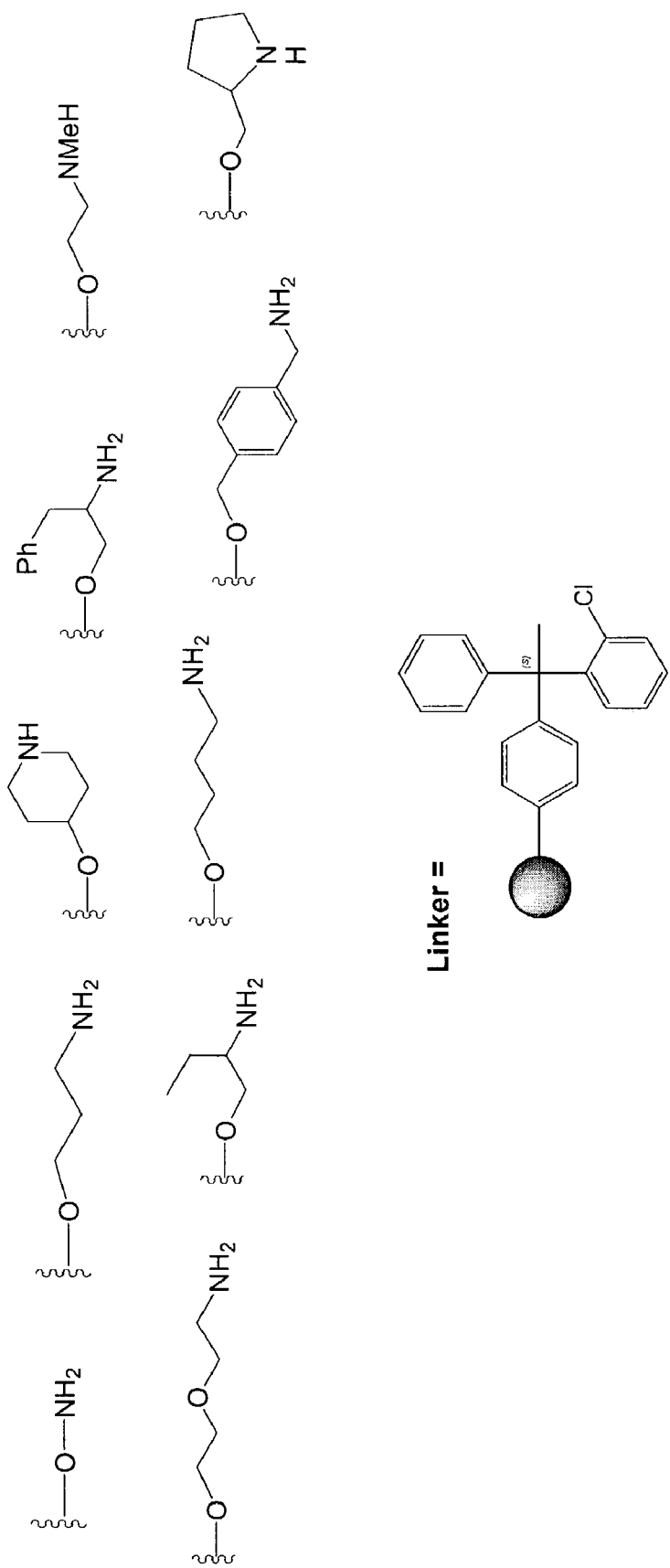
Figure 4:
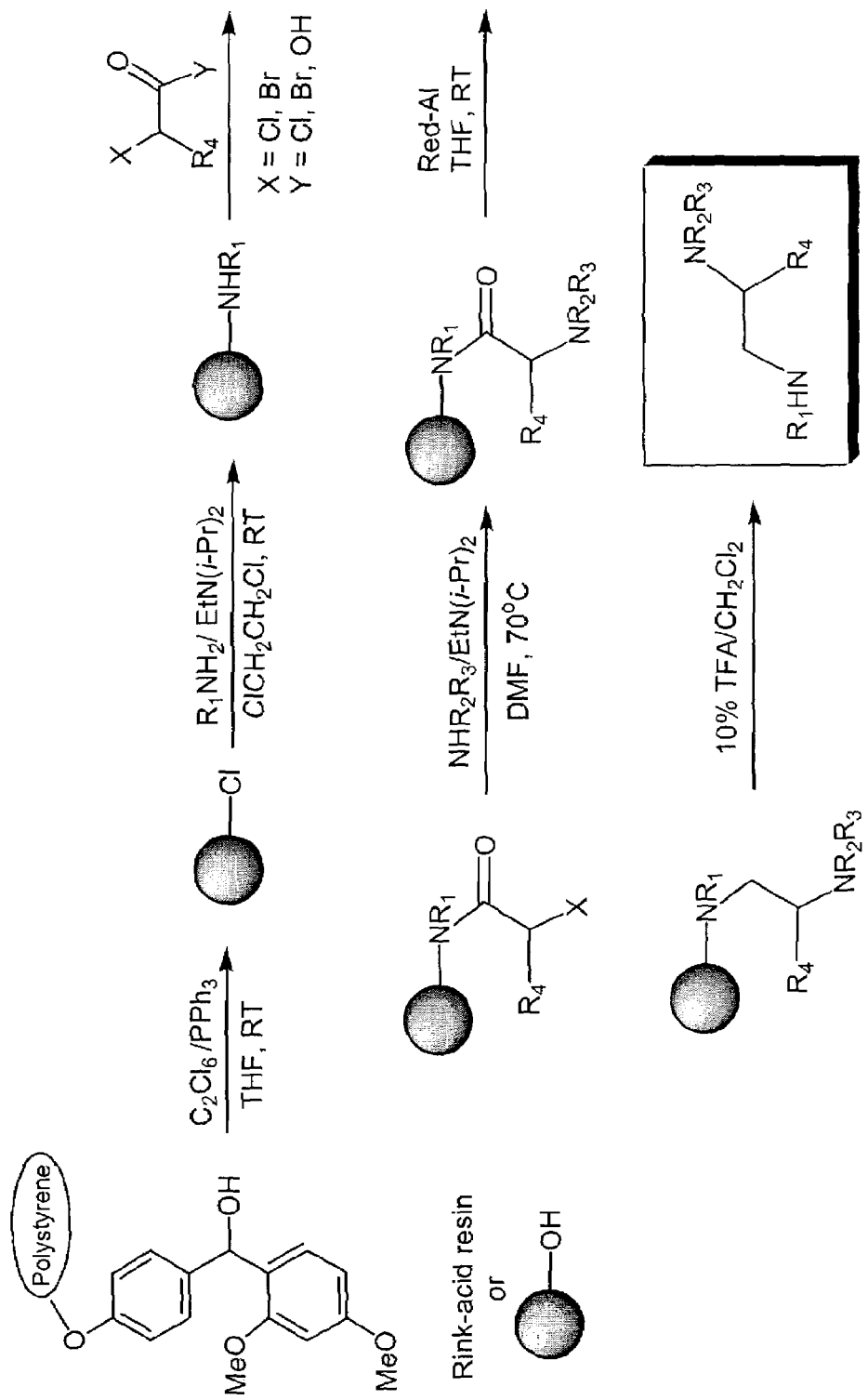
Figure 5:
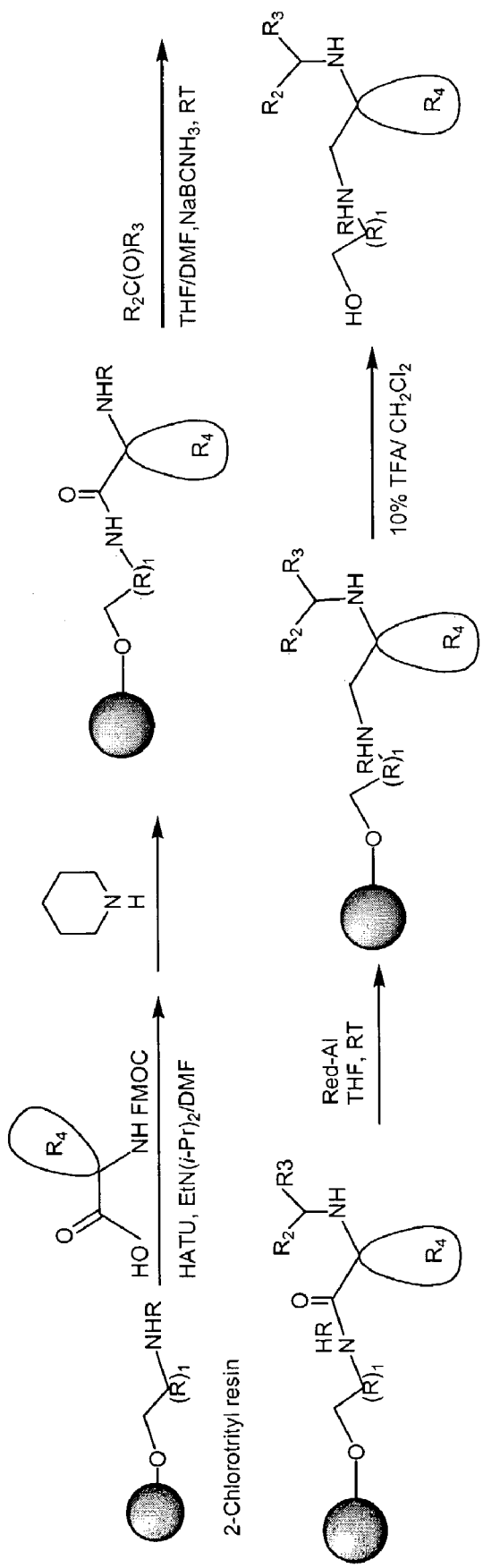

Deng, L., et al., "Recognition of Multiple Effects of Ethambutol on Metabolism of Mycobacterial Cell Envelope," Antimicrob. Agents Chemother., 1995, vol. 39, No. 3, pp. 694-701.

Dye, C., et al., "Global Burden of Tuberculosis: Estimated Incidence, Prevalence, and Mortality by Country," J. Am. Med. Assoc., 1999, vol. 282, No. 7, pp. 677-686.

Farmer, P., et. al., "The Dilemma of MDR-TB in the Global Era," Int. J. Tuberc. Lung Dis., 1998, vol. 2, No. 11, pp. 869-876.

Garigipati, R.S., Reagents for Combinatorial Organic Synthesis: Preparation and Uses of Rink-Chloride, Tetrahedron Lett., 1997, vol. 38, No. 39, pp. 6807-6810.

Gordon, D.W., et. al., "Reductive Alkylation on a Solid Phase: Synthesis of a Piperazinedione Combinatorial Library," Bioorg. Med. Chem. Lett., 1995, vol. 5, No. 1, pp. 47-50.

Gustafson, G.R., et. al., "Incorporation of Carbohydrates and Peptides into Large Triazine-Based Screening Libraries Using Automated Parallel Synthesis," Tetrahedron, 1998, vol. 54, p. 4051-4065.

Häusler, H., et al., "Ethambutol Analogues as Potential Antimycobacterial Agents," Bioorg. Med. Chem. Lett., 2001, vol. 11, pp. 1679-1681.

Lee, M.H., et. al., "Site-Specific Integration of Mycobacteriophage L5: Integration-Proficient Vectors for *Mycobacterium smegmatis, Mycobacterium tuberculosis*, and bacilli Calmette-Guerin," Proc. Natl. Acad. Sci. USA, 1991, vol. 88, pp. 3111-3115.

Lee, R.E., et. al., "Synthesis of the Mycobacterial Arabinose Donor β-D-Arabinofuranosyl-1-monophosphoryldecaprenol, Development of a Basic Arabinosyl-Transferase Assay, and Identification of Ethambutol as and Arabinosyl Transferase Inhibitor," J. Am. Chem. Soc., 1995, vol. 117, pp. 11829-11832.

Liu, G., et. al., "A General Solid-Phase Syntheses Strategy for the Preparation of 2-Pyrrolidinemethanol Ligands," J. Org. Chem., 1995, vol. 60, pp. 7712-7713.

March, J., "Advanced Organic Chemistry: Reactions, Mechanisms, and Structure," 3$^{rd}$ ed., John Wiley and Sons, New York, p. 916.

O'Brien, R.J., "Scientific Blueprint for Tuberculosis Drug Development," The Global Alliance for TB Drug Development, Inc., 2001.

Pablos-Mendez, A., et. al., "Global Surveillance for Antituberculosis-Drug Resistance," 1994-1997, N. Engl. J. Med., 1998, vol. 338, No. 23, pp. 1641-1649.

Rink, H., "Solid-Phase Synthesis of Protected Peptide Fragments Using a Trialkoxy-Diphenyl-Methylester Resin," Tetrahedron Lett., 1987, vol. 28, No. 33, pp. 3787-3790.

Shawar, R.M., at al., "Rapid Screening of Natural Products for Antimycobacterial Activity by Using Luciferase-Expressing Strains of *Mycobacterium bovis* BCG and *Mycobacterium intracellular*," Antimicrob. Agents Chemother., 1997, vol. 41, No. 3, pp. 570-574.

Shepherd, R.G., et al., "Structure-Activity Studies Leading to Ethambutol, a New Type of Antituberculous Compound," Ann. N.Y. Acad. Sci., 1966, vol. 135, pp. 686-710.

Silen, J.L., et al., "Screening for Novel Antimicrobials from Encoded Combinatorial Libraries by Using a Two-Dimensional Agar Format," Antimicrob. Agents Chemother., 1998, vol. 42, No. 6, pp. 1447-1453.

Sterling, T.R., Chemical Abstracts 131:281083, abstract of AIDS, vol, 13 (14), pp. 1899-1904, 1999.

Telenti, A., et al., "The *Emb* Operon, a Gene Cluster of *Mycobacterium tuberculosis* Involved in Resistance to Ethambutol," Natural Medicine, 1997, vol. 3, No. 5, pp. 567-570.

Zuckermann, R.N., et al., "Efficient Method for the Preparation of Peptoids [Oligo(N-substituted glycines)] by Subrnonomer Solid-Phase Synthesis," J. Am. Chem. Soc., 1992, vol. 114, pp. 10646-10647.

EPO Search Report as cited in EP 04809706, *European Patent Office—Search Report*, p. 105, Jan. 23, 2009.

Benoit et al., Derivatives Aminoalcoyles de la Benzhydrylamine, *Annales Pharmaceutiques Francaises*, pp. 354-361, Apr. 1, 1953.

Cymerman-Craig, J et al., Chemical Constitution and Anti-Tuberculous Activity: Part II: Bases Possessing the Diphenyl Structure, *British Journal of Experimental Pathology*, vol. 36, pp. 254-260, Jan. 1, 1955.

Davis, Brian—USPTO, Notice of Allowance cited in U.S. Appl. No. 11/173,192, *USPTO Notice of Allowance*, pp. 1-5, Jul. 14, 2008.

Davis, Brian J.—PTO, Office Action issued in U.S. Appl. No. 11/145,499 on May 3, 2007, *U.S. PTO—Office Action*, pp. 1-4, May 3, 2007.

Davis, Brian J.—PTO, Office Action cited in U.S. Appl. No. 11/145,499 on Nov. 5, 2008, *U.S. PTO—Office Action*, pp. 4, Nov. 5, 2008.

Davis, Brian J.—PTO, Office Action cited in U.S. Appl. No. 11/145,499 on Dec. 14, 2007, *U.S. PTO—Office Action*, pp. 1-5, Dec. 14, 2007.

Davis, Brian J.—PTO, Office Action cited in U.S. Appl. No. 11/145,499 on May 1, 2008, *U.S. PTO—Office Action*, pp. 1-4, May 1, 2008.

Hamilton-Miller, J.M.T., Inhibition of *Candida* by Compounds which Inhibit Cholesterol Biosynthesis, *Chemotherapy*, vol. 18, pp. 154-161, Jan. 1, 1973.

Jagoe, Donna A.—USPTO, Office Action cited in U.S. Appl. No. 10/936,217 on Jun. 25, 2008, *U.S. PTO—Office Action*, pp. 1-10, Jun. 25, 2008.

Murray et al., Chapter 22 Mycobacterium, *Medical Microbiology*, pp. 219-230, Jan. 1, 1990.

Roark, W. et al., Bioisosterism in Drug Design: Identification of and Structure-Activity Relationships in a Series of Glycine Anilide ACAT Inhibitors, *Bioorganic & Medicinal Chemistry Letters*, vol. 3(1), pp. 29-39, Jan. 1, 1995.

| Linker | Yield, % | Number of active mixtures | Number of hits | Hits active in both assays |
|---|---|---|---|---|
| Acid chlorides | | | | |
| Acetyl chloride | 66 | 0 | 0 | 0 |
| Acetyl chloride | 58 | 0 | 0 | 0 |
| 3-Chloropropionyl chloride | 20 | 0 | 0 | 0 |
| Amino acids | | | | |
| Leu-OH | 31-52 | 8 | 1 | 0 |
| Trp-OH | 47-49 | 16 | 5 | 1 |
| Cha-OH | 68-80 | 24 | 3 | 2 |
| 1-Amino-1-cyclopentane crb. Acid | 66 | 8 | 1 | 0 |
| Phe-(2-Cl)-OH | 82-85 | 16 | 6 | 3 |
| His-OH | 57-68 | 16 | 2 | 0 |
| Amc-OH | 96 | 16 | 29 | 9 |
| Met-OH | 70-79 | 7 | 5 | 1 |
| Ile-OH | 64-80 | 9 | 11 | 2 |
| Ser-OH | 83 | 16 | 9 | 2 |
| Phe-OH | 64 | 16 | 18 | 4 |
| Pro-OH | 62 | 8 | 1 | 0 |
| Arg-OH | 20 | 8 | postponed | 0 |
| Thi-OH | 88 | 8 | 15 | 5 |
| Inp-OH | 72 | 16 | 9 | 9 |
| Thz-OH | ~20 | 0 | 0 | 0 |
| Tic-OH | ~40 | 6 | 1 | 0 |
| *Total actives* | | 198 | 118 | 38 |
| The number of the plates | | 20 | | |

FIGURE 3

Phenylalanine
Leucine
Isoleucine
Tryptophan
Serine
Cyclohexylalanine
Methionine
Arginine
Histidine
Isonipecotic acid
4-Aminomethyl cyclohexane carboxylic acid
Tetrahydroisoquinoline-3-carboxylic acid
2-Chlorophenylalanine
Thiazoline carboxylic acid
Proline
Thienylalanine
1-Amino-1-Cyclopentanecarboxylic acid

FIGURE 7

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 501 | 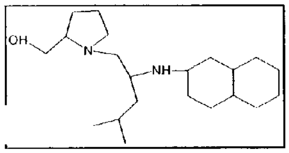 | 25 | | | | 1.85 | | 35.5 | 102 | 12-127 |
| 502 | 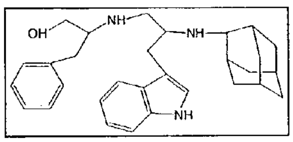 | 25 | | | | 1.55 | | 60.08 | 98 | 12-132-1 |
| 503 | 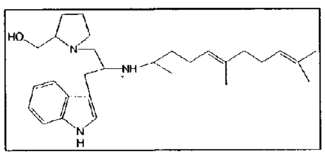 | 6.25 | | | | 0.83 | | 51.29 | 104 | 12-132-2 |
| 504 | 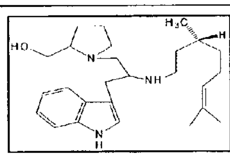 | 6.25 | | | | 4.6 | 7.37+/-0.37 | 51.29 | 35 | 12-132-2 |
| 505 | 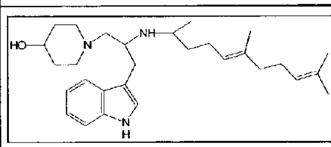 | 25 | | | | 1.7 | | 51.29 | 104 | 12-132-2 |
| 506 | 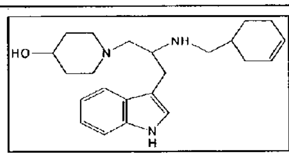 | 50 | | | | 1.6 | | 51.29 | 92 | 12-132-2 |
| 507 | 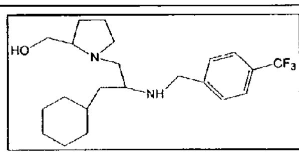 | 12.5 | | | | 3 | | 35.5 | 94 | 12-133-3 |
| 508 | 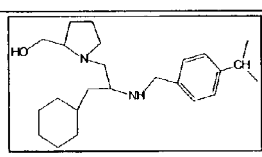 | 12.5 | 15.63 | 59 | 3.78 | 5 | 6.07+/-0.43 | 35.5 | 68 | 12-133-3 |

Figure 11B:
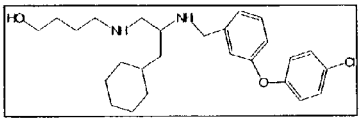
Figure 11B:
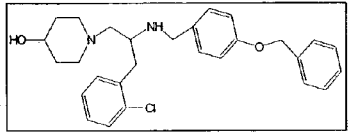
Figure 11B:
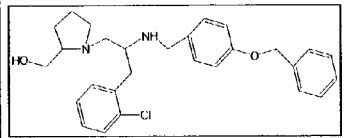
Figure 11B:
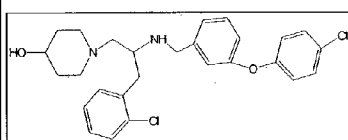
Figure 11B:
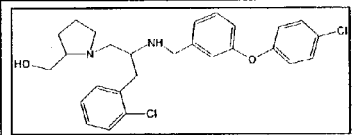
Figure 11B:
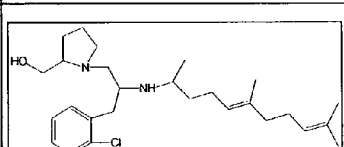
Figure 11B:
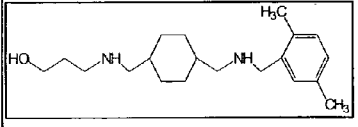
Figure 11B:
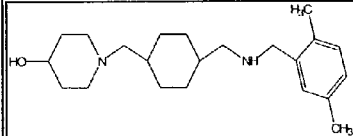
Figure 11E:
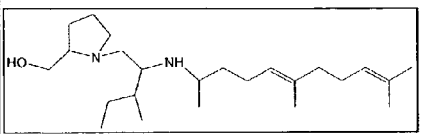
Figure 11E:
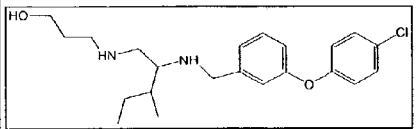
Figure 11E:
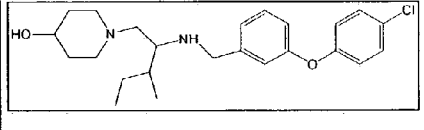
Figure 11E:
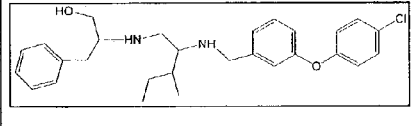
Figure 11E:
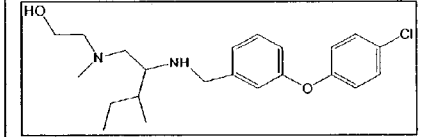
Figure 11E:
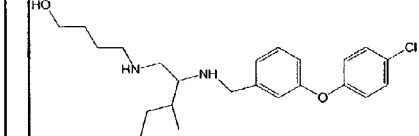
Figure 11E:
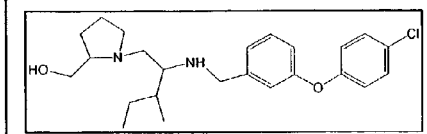
Figure 11E:
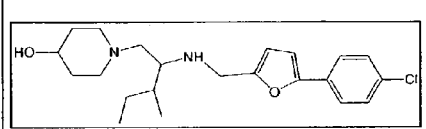
Figure 11F:
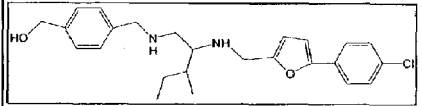
Figure 11F:
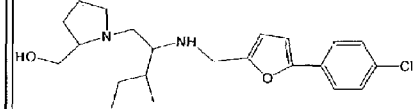
Figure 11F:
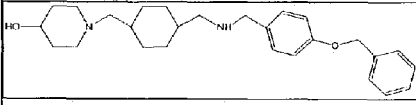
Figure 11F:
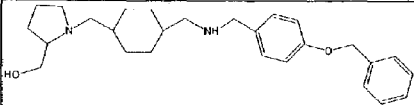
Figure 11F:
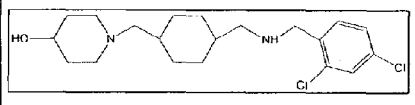
Figure 11F:
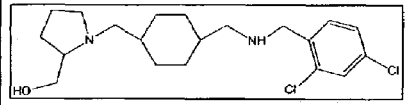
Figure 11F:
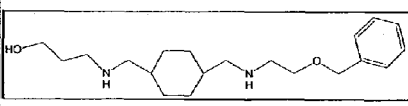
Figure 11F:
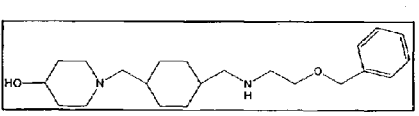
Figure 11G:
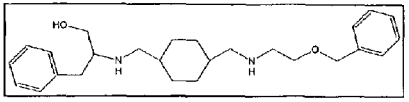
Figure 11G:
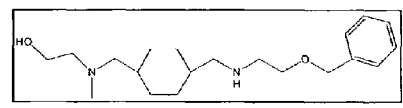
Figure 11G:
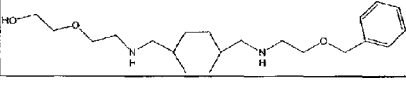
Figure 11G:
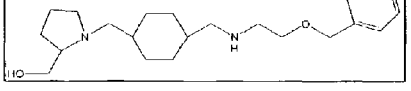
Figure 11G:
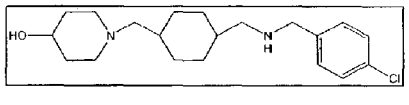
Figure 11G:
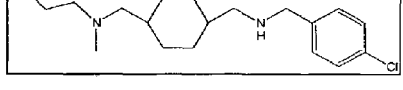
Figure 11G:
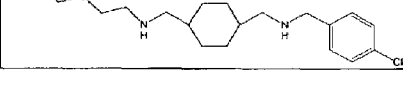
Figure 11G:
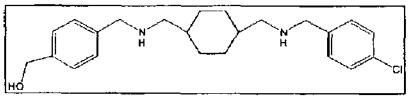
Figure 11H:
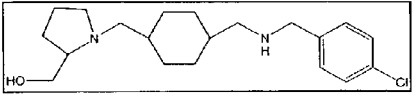
Figure 11H:
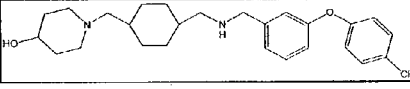
Figure 11H:
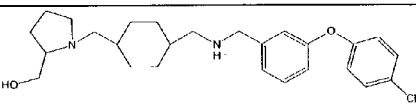
Figure 11H:
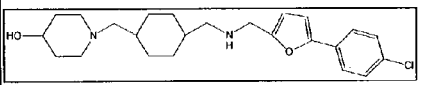
Figure 11H:
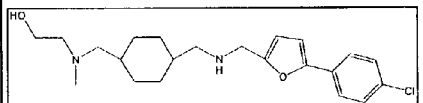
Figure 11H:
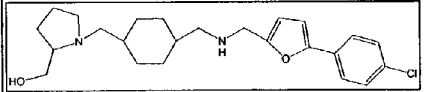
Figure 11H:
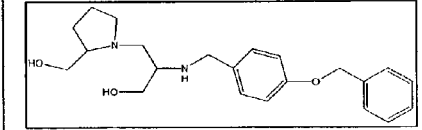
Figure 11H:
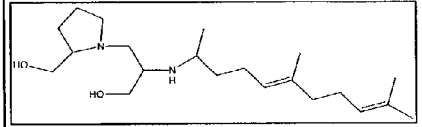
Figure 11I:
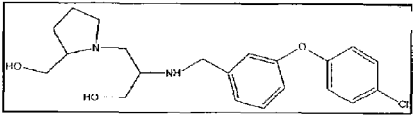
Figure 11I:
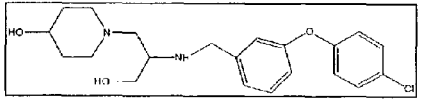
Figure 11I:
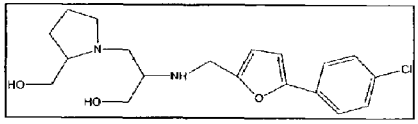
Figure 11I:
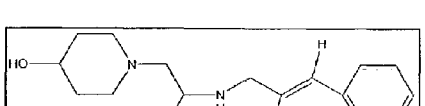
Figure 11I:
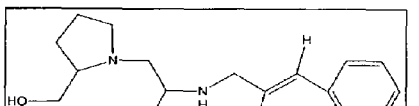
Figure 11I:
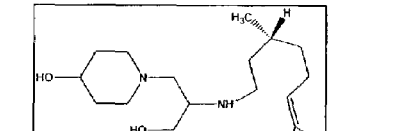
Figure 11I:
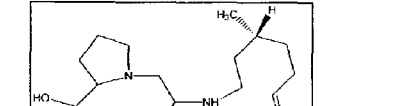
Figure 11I:
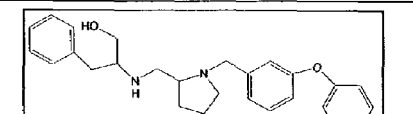
Figure 11J:
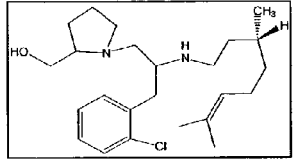
Figure 11J:
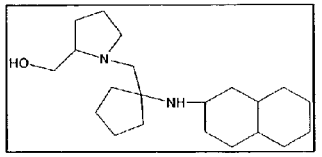
Figure 11J:
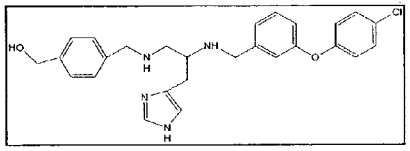
Figure 11J:
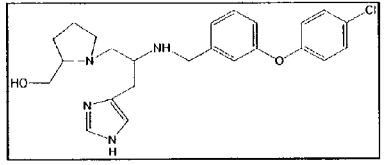
Figure 11J:
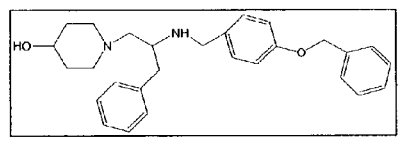
Figure 11J:
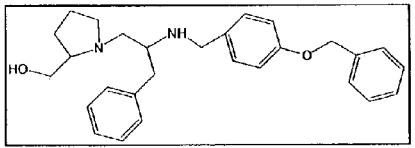
Figure 11J:
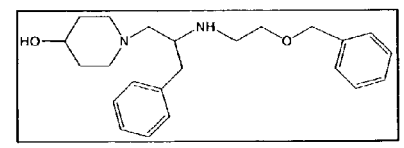
Figure 11J:
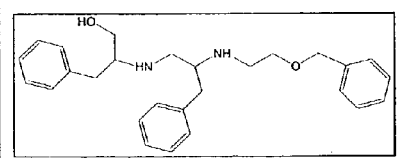
Figure 11K:
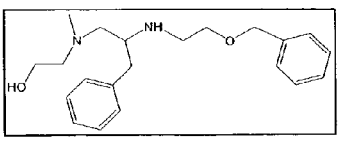
Figure 11K:
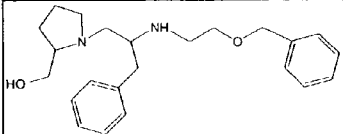
Figure 11K:
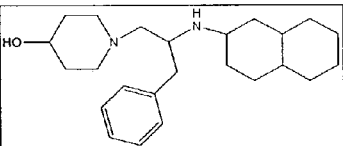
Figure 11K:
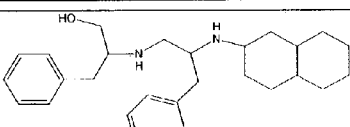
Figure 11K:
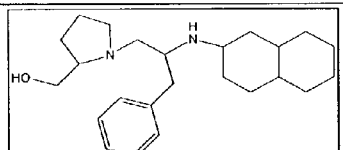
Figure 11K:
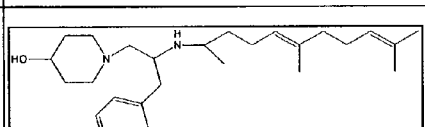
Figure 11K:
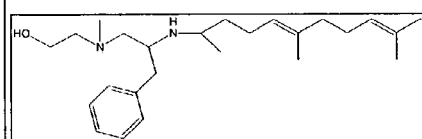
Figure 11K:
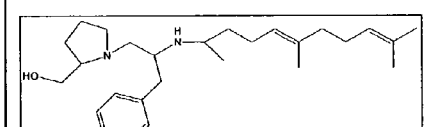
Figure 11L:
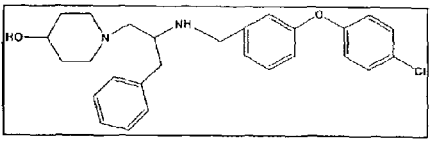
Figure 11L:
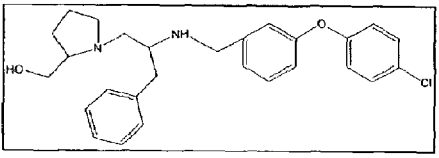
Figure 11L:
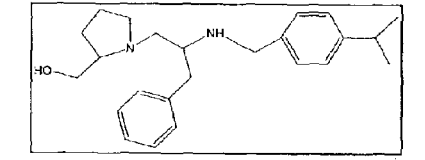
Figure 11L:
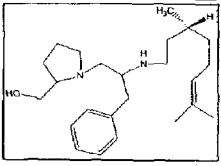
Figure 11L:
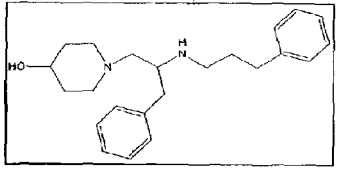
Figure 11L:
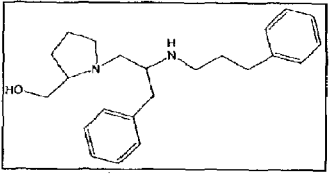
Figure 11L:
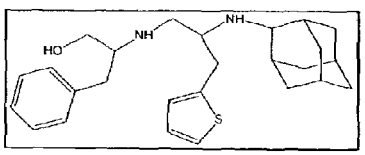
Figure 11L:
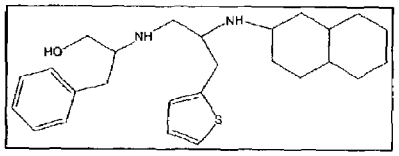
Figure 11O:
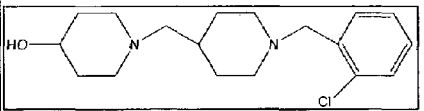
Figure 11O:
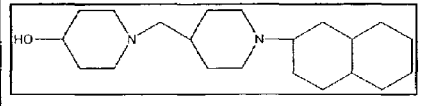
Figure 11O:
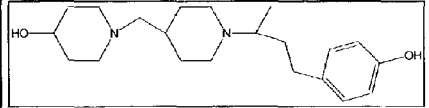
Figure 11O:
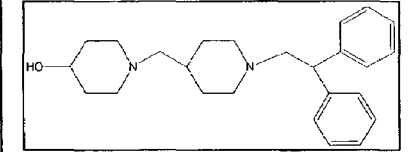
Figure 11O:
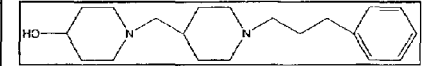
Figure 11O:
Figure 11O:
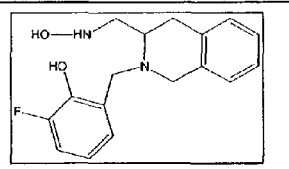

FIGURE 11(a)

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 509 | 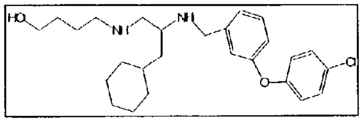 | 12.5 | | | | 0.8 | | 53.52 | 32 | 12-133-3 |
| 510 | 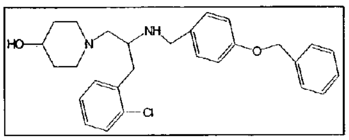 | 12.5 | 62.5 | | | 1.3 | 4.91+/-0.45 | | 26 | 12-141-A |
| 511 | 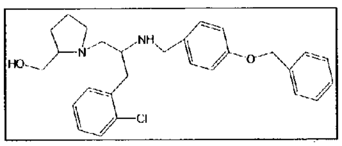 | 25 | 62.5 | | | 4.4 | 5.88+/-0.49 | | 26 | 12-141-A |
| 512 | 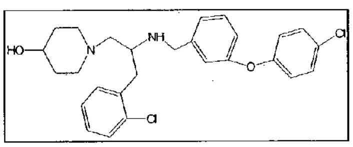 | 12.5 | 31.25 | | | 1.3 | 5.93+/-0.53 | | 32 | 12-141-A |
| 513 | 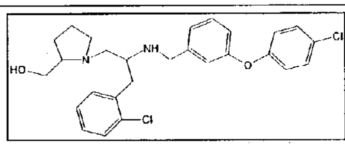 | 12.5 | 15.63 | | | 10 | 6.9+/-0.57 | | 32 | 12-141-A |
| 514 | 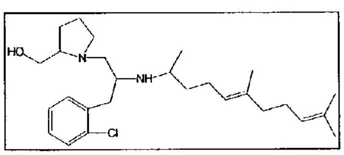 | 25 | | | | 44 | 7.79+/-0.46 | | 104 | 12-141-A |
| 515 | 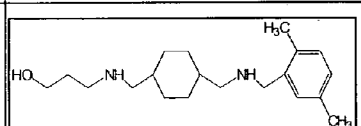 | 25 | | | | 1.7 | | | 45 | 12-143-B |
| 516 | 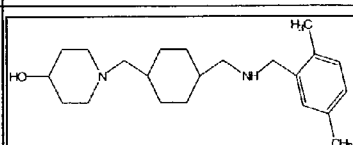 | 3.13 | >500 | | | 2.07 | 3.71+/-0.3 | | 45 | 12-143-B |

| # | Structure | MIC | MIC exper. | LD50 (uM) | SI | Lux | LogP | TPSA | Frag. #2 | Original plate # |
|---|---|---|---|---|---|---|---|---|---|---|
| Amino alcohol pre-loaded resins | | | | | | | | | | |
| 517 | 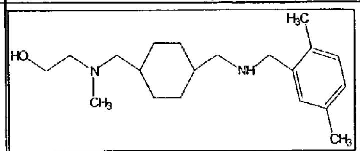 | 6.25 | | | | 2.33 | 3.91+/-0.27 | | 45 | 12-143-B |
| 518 | 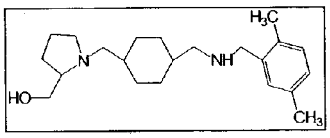 | 3.13 | 500 | | | 2.23 | 4.68+/-0.36 | | 45 | 12-143-B |
| 518Dbl | 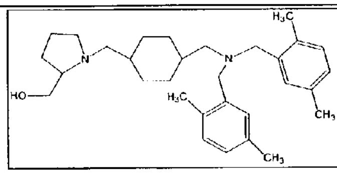 | 3.13 | 7.8 | | | 2.23 | | | 45 | |
| 519 | 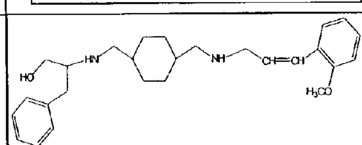 | 12.5 | | | | 1.27 | | | 70 | 12-143-B |
| 520 | 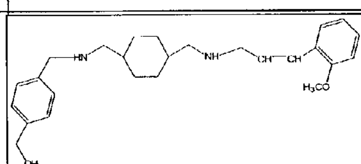 | 12.5 | | | | 1.17 | | | 70 | 12-143-B |
| 521 | 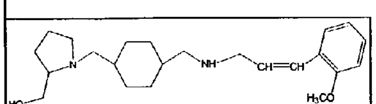 | 12.5 | | | | 1.12 | | | 70 | 12-143-B |
| 522 | 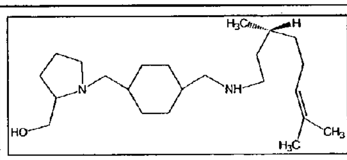 | 12.5 | | | | 1.74 | | | 35 | 12-143-B |
| 523 | 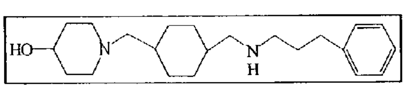 | 6.25 | 250 | | | 1.66 | 2.91+/-0.3 | | 59 | 12-143-B |

FIGURE 11(c)

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 524 | 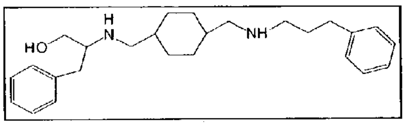 | 12.5 | | | | 1.3 | | | 59 | 12-143-B |
| 525 | 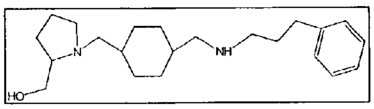 | 6.25 | | | | 1.62 | 4.8+/-0.37 | | 59 | 12-143-B |
| 526 | 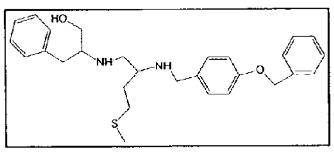 | 12.5 | | | | 1 | | | 26 | 12-144-A |
| 527 | 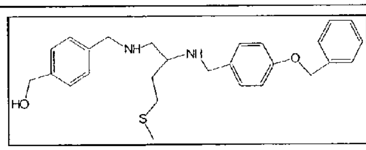 | 12.5 | | | | 1 | | | 26 | 12-144-A |
| 528 | 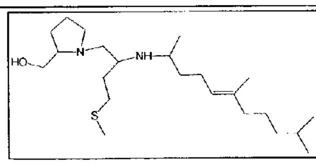 | 12.5 | | | | 5.85 | | | 104 | 12-144-A |
| 529 | 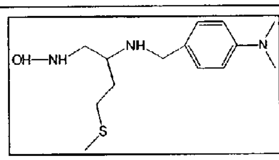 | 25 | | | | 1.2 | | | 44 | 12-144-A |
| 530 | 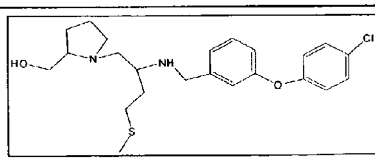 | 12.5 | | | | 0.8 | | | 32 | 12-144-A |
| 531 | 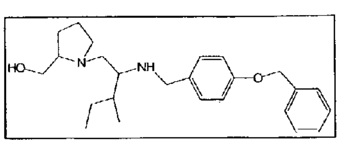 | 12.5 | | | | 1.7 | | | 26 | 12-149a |

FIGURE 11(d)

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 532 | 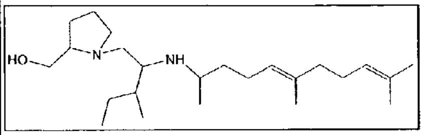 | 12.5 | | | | 8.1 | | | 104 | 12-149a-1 |
| 533 | 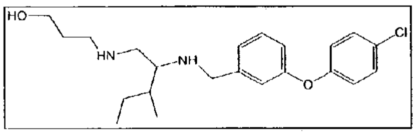 | 12.5 | | | | 1.04 | | | 32 | 12-149a-1 |
| 534 | 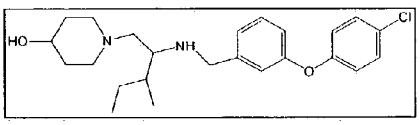 | 12.5 | | | | 1.25 | | | 32 | 12-149a-1 |
| 535 | 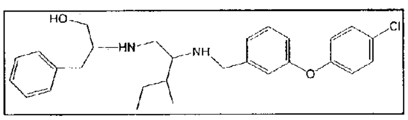 | 12.5 | | | | 0.92 | | | 32 | 12-149a-1 |
| 536 | 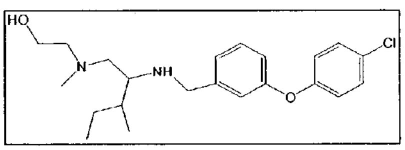 | 6.25 | | | | 1.14 | | | 32 | 12-149a-1 |
| 537 | 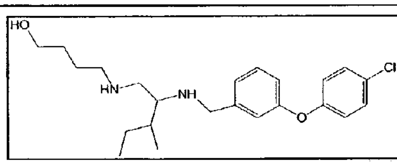 | 12.5 | | | | 0.82 | | | 32 | 12-149a-1 |
| 538 | 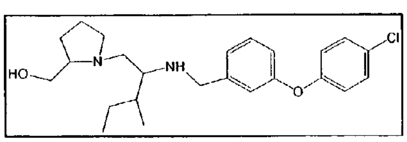 | 6.25 | 31.25 | | | 3.8 | 6.14+/-0.54 | | 32 | 12-149a-1 |
| 539 | 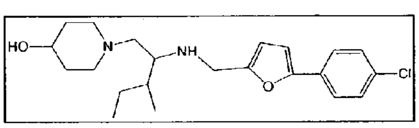 | 12.5 | | | | 1.12 | | | 33 | 12-149a-1 |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 540 | 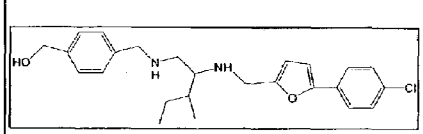 | 12.5 | | | | 0.65 | | | 33 | 12-149a-1 |
| 541 | 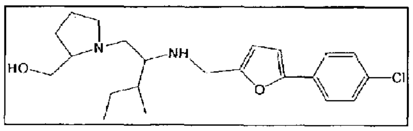 | 6.25 | | | | 1.15 | | | 33 | 12-149a-1 |
| 542 | 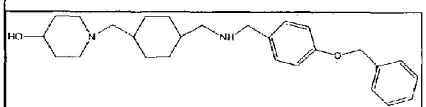 | 3.13 | 500 | | | 1.7 | | | 26 | 12-143-A |
| 543 | 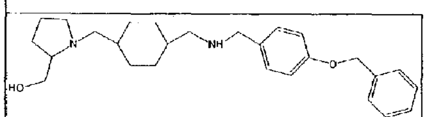 | 6.25 | | | | 1.38 | 5.33+/-0.38 | | 26 | 12-143-A |
| 544 | 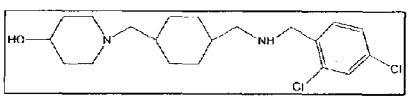 | 12.5 | | | | 1.87 | | | 38 | 12-143-A |
| 545 | 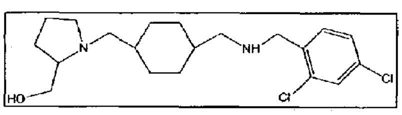 | 12.5 | | | | 1.8 | | | 38 | 12-143-A |
| 546 | 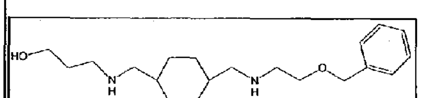 | 12.5 | | | | 1.17 | | | 27 | 12-143-A |
| 547 | 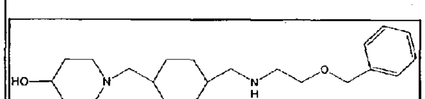 | 6.25 | | | | 1.64 | 2.81+/-0.64 | | 27 | 12-143-A |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 548 | 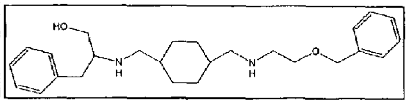 | 12.5 | | | | 1.45 | | | 27 | 12-143-A |
| 549 | 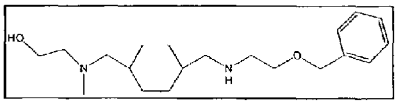 | 6.25 | | | | 1.42 | | | 27 | 12-143-A |
| 550 | 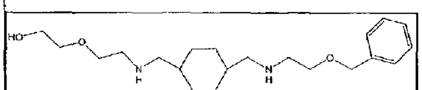 | 25 | | | | 1.5 | | | 27 | 12-143-A |
| 551 | 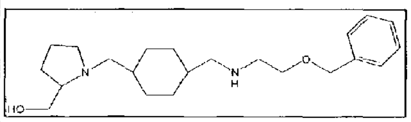 | 6.25 | | | | 1.25 | | | 27 | 12-143-A |
| 552 | 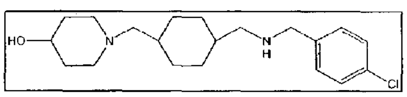 | 6.25 | | | | 3 | 3.39+/-0.31 | | 29 | 12-143-A |
| 553 | 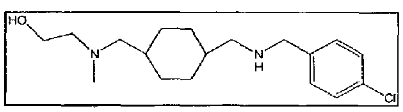 | 12.5 | | | | 1.5 | | | 29 | 12-143-A |
| 554 | 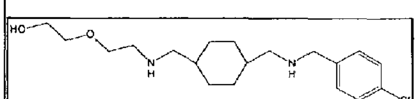 | 25 | | | | 7.87 | | | 29 | 12-143-A |
| 555 | 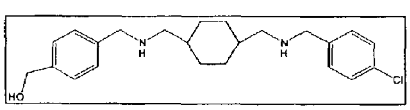 | 12.5 | | | | 1.26 | | | 29 | 12-143-A |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 556 | 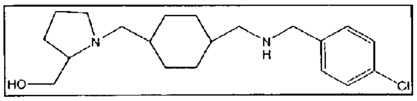 | 6.25 | | | | 2.86 | | | 29 | 12-143-A |
| 557 | 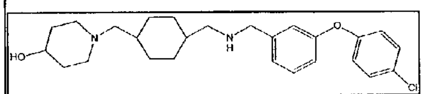 | 12.5 | | | | 1.14 | | | 32 | 12-143-A |
| 558 | 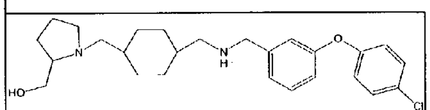 | 12.5 | | | | 1 | | | 32 | 12-143-A |
| 559 | 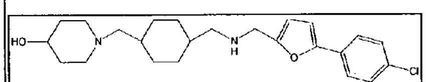 | 3.13 | 125 | | | 0.9 | | | 33 | 12-143-A |
| 560 | 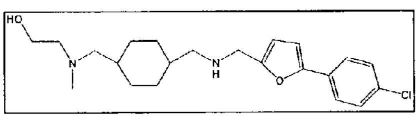 | 12.5 | | | | 0.9 | | | 33 | 12-143-A |
| 561 | 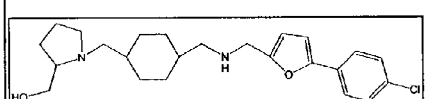 | 3.13 | 250 | | | 1.14 | | | 33 | 12-143-A |
| 562 | 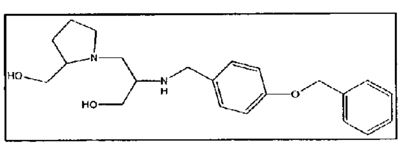 | 25 | | | | 0.78 | | | 26 | 12-149b-1 |
| 563 | 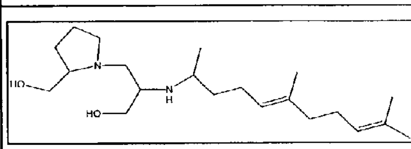 | 25 | | | | 2.4 | | | 104 | 12-149b-2 |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 564 | 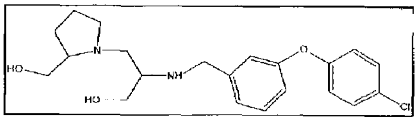 | 12.5 | | | | 1.56 | | | 32 | 12-149b-2 |
| 565 | 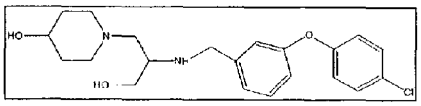 | 12.5 | | | | 1.45 | | | 32 | 12-149b-2 |
| 566 | 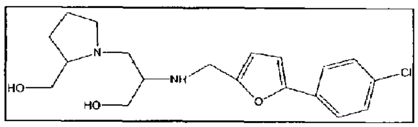 | 6.25 | | | | 4.5 | | | 33 | 12-149b-2 |
| 567 | 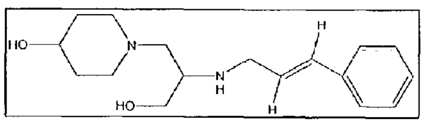 | 12.5 | | | | 1.29 | | | 34 | 12-149b-2 |
| 568 | 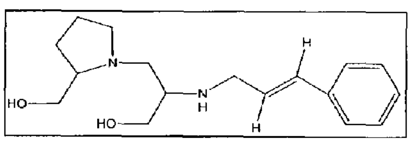 | 12.5 | | | | 0.89 | | | 34 | 12-149b-2 |
| 569 | 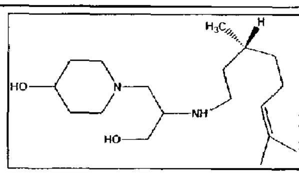 | 12.5 | | | | 1.27 | | | 35 | 12-149b-2 |
| 570 | 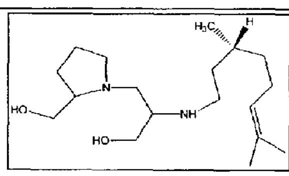 | 12.5 | | | | 1 | | | 35 | 12-149b-2 |
| 571 | 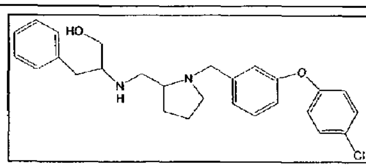 | 25 | | | | 1.3 | | | 32 | 12-149d-1 |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 572 | 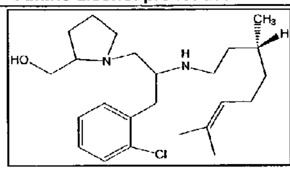 | 6.25 | 31.25 | | | 8.5 | | | 35 | 12-141-B |
| 573 | 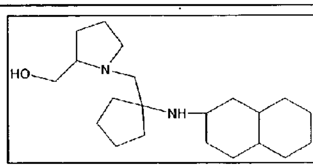 | 25 | | | | 1.12 | | | 102 | 12-140-1 |
| 574 | 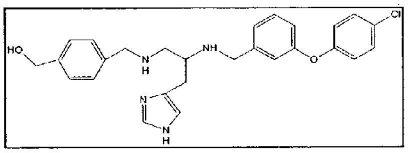 | 25 | | | | 0.9 | | | 32 | 12-142-2 |
| 575 | 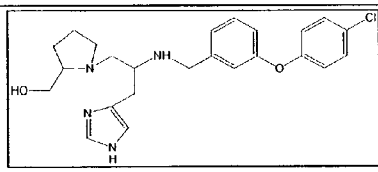 | 25 | | | | 0.79 | | | 32 | 12-142-2 |
| 576 | 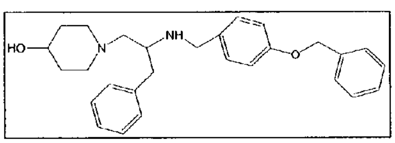 | 25 | | | | 2 | | | 26 | 12-149c-1 |
| 577 | 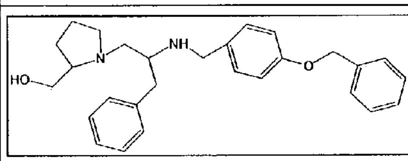 | 12.5 | | | | 1.35 | | | 26 | 12-149c-1 |
| 578 | 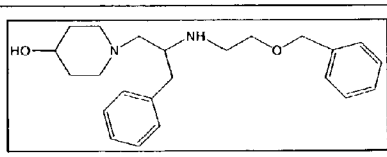 | 25 | | | | 1.54 | | | 27 | 12-149c-1 |
| 579 | 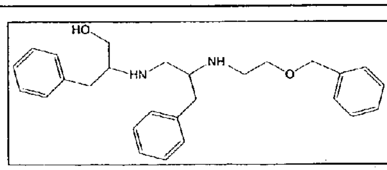 | 25 | | | | 1 | | | 27 | 12-149c-1 |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 580 | 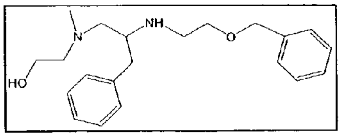 | 25 | | | | 1.1 | | | 27 | 12-149c-1 |
| 581 | 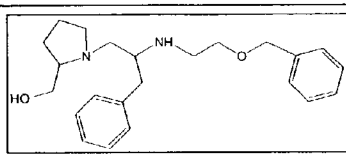 | 12.5 | | | | 0.87 | | | 27 | 12-149c-1 |
| 582 | 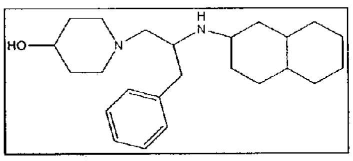 | 25 | | | | 1.42 | | | 102 | 12-149c-1 |
| 583 | 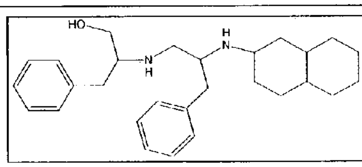 | 25 | | | | 1 | | | 102 | 12-149c-1 |
| 584 | 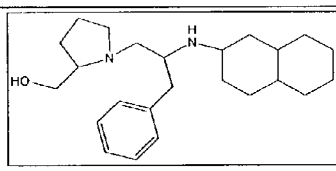 | 12.5 | | | | 0.96 | | | 102 | 12-149c-1 |
| 585 | 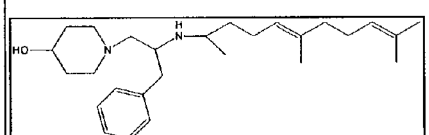 | 25 | | | | 1.19 | | | 104 | 12-149c-1 |
| 586 | 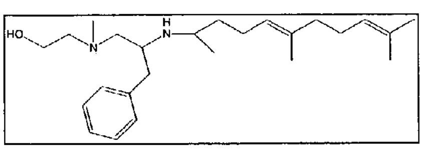 | 25 | | | | 1.2 | | | 104 | 12-149c-1 |
| 587 | 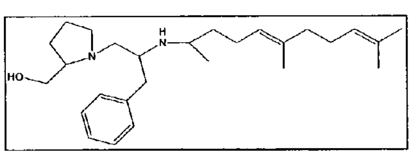 | 6.25 | | | | 6.39 | | | 104 | 12-149c-1 |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 588 | 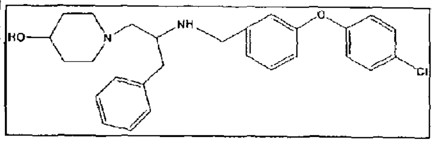 | 6.25 | | | | 1.2 | | | 32 | 12-149c-2 |
| 589 | 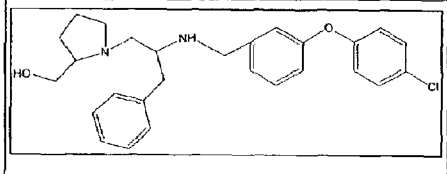 | 3.13 | L 31.25 D- 15.63 | | | 1.75 | | | 32 | 12-149c-2 |
| 590 | 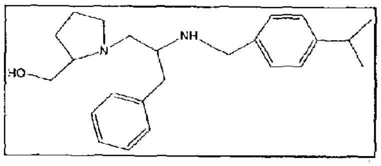 | 12.5 | | | | 2.46 | | | 68 | 12-149c-2 |
| 591 | 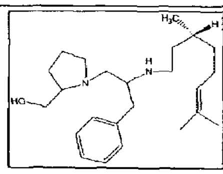 | 12.5 | | | | 3.45 | | | 35 | 12-149c-2 |
| 592 | 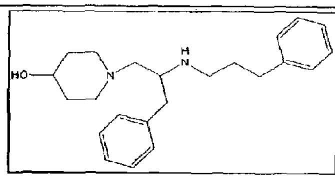 | 12.5 | | | | 1.27 | | | 59 | 12-149c-2 |
| 593 | 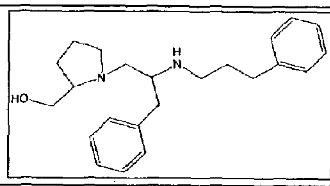 | 12.5 | | | | 0.76 | | | 59 | 12-149c-2 |
| 594 | 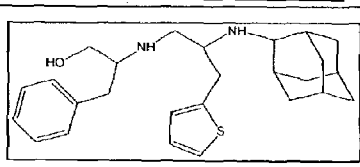 | 12.5 | | | | 0.88 | | | 98 | 12-156b-1 |
| 595 | 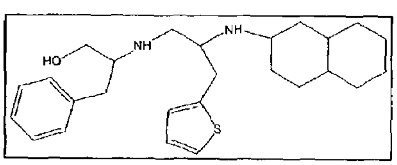 | 12.5 | | | | 1.9 | | | 102 | 12-156b-1 |

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 596 | 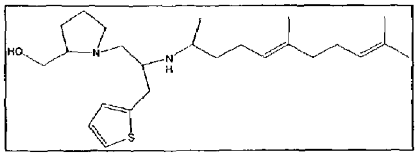 | 6.25 | | | | 26.4 | 6.88+/-0.47 | | 104 | 12-156b-1 |
| 597 | 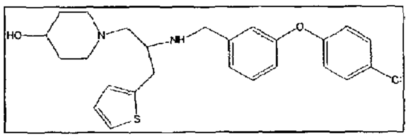 | 6.25 | | | | 2.2 | 5.02+/-0.54 | | 32 | 12-156b-1 |
| 598 | 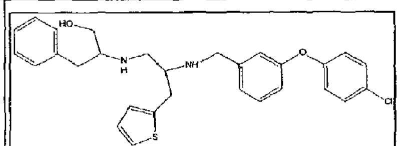 | 12.5 | | | | 0.9 | | | 32 | 12-156b-1 |
| 599 | 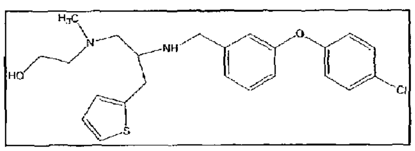 | 12.5 | | | | 2.1 | | | 32 | 12-156b-1 |
| 600 | 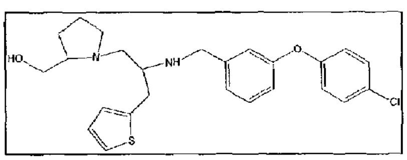 | 6.25 | | | | 2.86 | 5.98+/-0.58 | | 32 | 12-156b-1 |
| 601 | 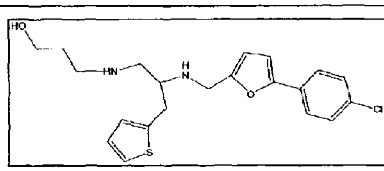 | 12.5 | | | | 1.58 | | | 33 | 12-156b-1 |
| 602 | 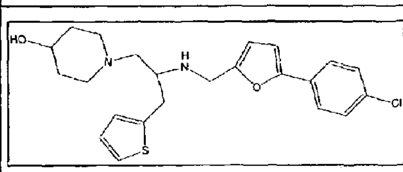 | 6.25 | | | | 1.37 | 4.07+/-0.51 | | 33 | 12-156b-1 |
| 603 | 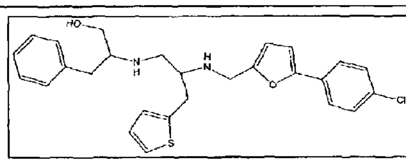 | 12.5 | | | | 0.82 | | | 33 | 12-156b-1 |

FIGURE 11(m)

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 604 | 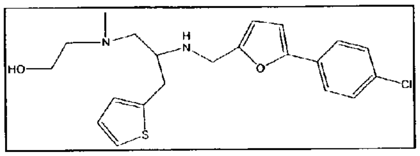 | 12.5 | | | | 0.87 | | | 33 | 12-156b-1 |
| 605 | 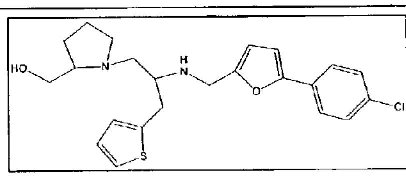 | 3.13 | 62.5 | | | 4.3 | | | 33 | 12-156b-1 |
| 606 | 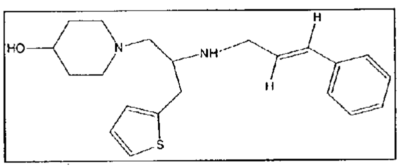 | 6.25 | | | | 1.43 | | | 34 | 12-156b-1 |
| 607 | 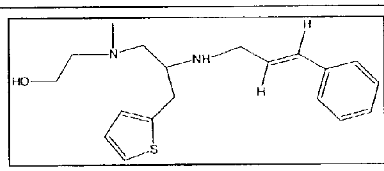 | 12.5 | | | | 1.3 | | | 34 | 12-156b-1 |
| 608 | 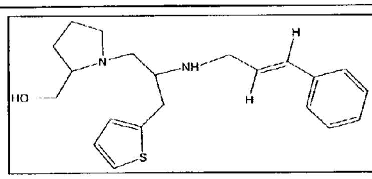 | 12.5 | | | | 0.89 | | | 34 | 12-156b-1 |
| 609 | 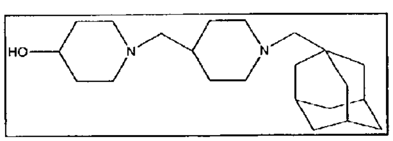 | 25 | 7.8 | 56 | 7.18 | 55.76 | 3.76+/-0.36 | | 1 | 12-156c-1 |
| 610 | 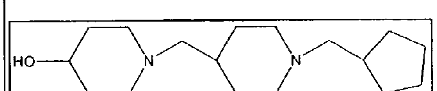 | 50 | 125 | | | 26.3 | 2.37+/-0.32 | | 3 | 12-156c-1 |
| 611 | 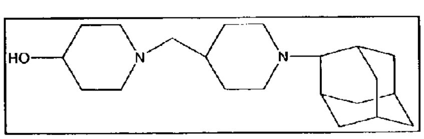 | 12.5 | 31.25 | | | 97.25 | 3.24+/-0.34 | | 98 | 12-156c-1 |

FIGURE 11(n)

| # | Structure | MIC | MIC exper. | LD50 (uM) | SI | Lux | LogP | TPSA | Frag. #2 | Original plate # |
|---|---|---|---|---|---|---|---|---|---|---|
| | Amino alcohol pre-loaded resins | | | | | | | | | |
| 612 | 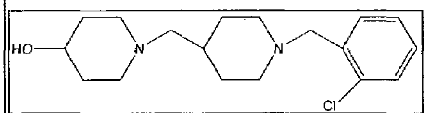 | 25 | 31.25 | | | 101.37 | 2.37+/-0.41 | | 28 | 12-156c-1 |
| 613 | 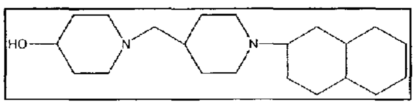 | 12.5 | 31.25 | | | 102.4 | 3.95+/-0.33 | | 102 | 12-156c-1 |
| 614 | 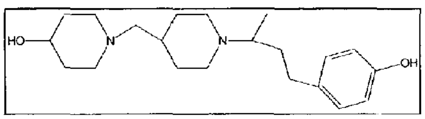 | 6.25 | 7.8 | | | 25.25 | 1.91+/-0.46 | 46.94 | 107 | 12-156c-1 |
| 615 | 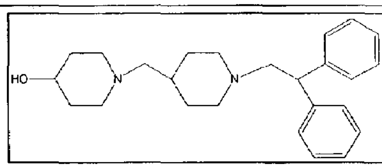 | 3.13 | 7.8 | 30 | 3.85 | 35 | 3.16+/-0.46 | | 47 | 12-156c-1 |
| 616 | 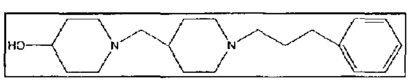 | 12.5 | 15.63 | | | 19.49 | 2.85+/-0.38 | | 59 | 12-156c 1 |
| 617 | 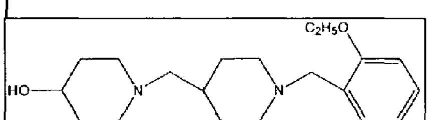 | 25 | 62.5 | | | 31.9 | 2.23+/-0.41 | | 48 | 12-156c-1 |
| 618 | 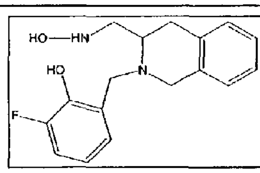 | 6.25 | | | | 0.9 | | | 55 | 12-166b-1 |

Table 3 Lay-out of Representative 96-Well Deconvolution Plate.

| A1 | A2 | A3 | A4 | A5 | A6 | A7 | A8 | A9 | A10 | Selected carb comp added to A1-A10 |
|---|---|---|---|---|---|---|---|---|---|---|
| B1 | B2 | B3 | B4 | B5 | B6 | B7 | B8 | B9 | B10 | Selected carb comp, added to B1-B10 |
| C1 | C2 | C3 | C4 | C5 | C6 | C7 | C8 | C9 | C10 | Selected carb comp, added to C1-C10 |
| D1 | D2 | D3 | D4 | D5 | D6 | D7 | D8 | D9 | D10 | Selected carb comp, added to D1-D10 |
| E1 | E2 | E3 | E4 | E5 | E6 | E7 | E8 | E9 | E10 | Selected carb comp, added to E1-E10 |
| F1 | F2 | F3 | F4 | F5 | F6 | F7 | F8 | F9 | F10 | Selected carb comp, added to F1-F10 |
| G1 | G2 | G3 | G4 | G5 | G6 | G7 | G8 | G9 | G10 | Selected carb comp, added to G1-G10 |
| H1 | H2 | H3 | H4 | H5 | H6 | H7 | H8 | H9 | H10 | Selected carb comp, added to H1-H10 |
| Resin #1 | Resin #2 | Resin #3 | Resin #4 | Resin #5 | Resin #6 | Resin #7 | Resin #8 | Resin #9 | Resin #10 | "X" selected carbonyl compounds to be added on the step 4<br><br>Individual resins ##1 through 10, pre-loaded with proper amine N1 |

FIGURE 12

METHODS OF USE AND COMPOSITIONS FOR THE DIAGNOSIS AND TREATMENT OF INFECTIOUS DISEASE

CROSS REFERENCE TO RELATED PATENT APPLICATIONS

The present application claims priority to U.S. Provisional Patent Application Serial No. 60/381,244 filed May 17, 2002. The present application is related to pending U.S. patent application Ser. No. 10/147,587 filed May 17, 2002.

FIELD OF INVENTION

The present invention relates to methods and compositions for treating disease caused by microorganisms, particularly tuberculosis. The present invention also relates to methods and compositions having improved anti-mycobacterial activity, namely compositions comprising novel substituted ethylene diamine compounds.

BACKGROUND OF THE INVENTION

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686, (1999); and 2000 WHO/OMS Press Release).

After decades of decline, TB is now on the rise. In the United States, up to 10 million individuals are believed to be infected. Almost 28,000 new cases were reported in 1990, constituting a 9.4 percent increase over 1989. A sixteen percent increase in TB cases was observed from 1985 to 1990. Overcrowded living conditions and shared air spaces are especially conducive to the spread of TB, contributing to the increase in instances that have been observed among prison inmates, and among the homeless in larger U.S. cities. Approximately half of all patients with "Acquired Immune Deficiency Syndrome" (AIDS) will acquire a mycobacterial infection, with TB being an especially devastating complication. AIDS patients are at higher risks of developing clinical TB, and anti-TB treatment seems to be less effective than in non-AIDS patients. Consequently, the infection often progresses to a fatal disseminated disease.

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

The World Health Organization (WHO) continues to encourage the battle against TB, recommending prevention initiatives such as the "Expanded Program on Immunization" (EPI), and therapeutic compliance initiatives such as "Directly Observed Treatment Short-Course" (DOTS). For the eradication of TB, diagnosis, treatment, and prevention are equally important. Rapid detection of active TB patients will lead to early treatment by which about 90% cure is expected. Therefore, early diagnosis is critical for the battle against TB. In addition, therapeutic compliance will ensure not only elimination of infection, but also reduction in the emergence of drug-resistance strains.

The emergence of drug-resistant *M. tuberculosis* is an extremely disturbing phenomenon. The rate of new TB cases proven resistant to at least one standard drug increased from 10 percent in the early 1980's to 23 percent in 1991. Compliance with therapeutic regimens, therefore, is also a crucial component in efforts to eliminate TB and prevent the emergence of drug resistant strains. Equally important is the development of new therapeutic agents that are effective as vaccines, and as treatments, for disease caused by drug resistant strains of mycobacteria.

Although over 37 species of mycobacteria have been identified, more than 95% of all human infections are caused by six species of mycobacteria: *M. tuberculosis, M. avium intracellulare, M. kansasii, M. fortuitum, M. chelonae*, and *M. leprae*. The most prevalent mycobacterial disease in humans is tuberculosis (TB) which is predominantly caused by mycobacterial species comprising *M. tuberculosis, M. bovis*, or *M. africanum* (Merck Manual 1992). Infection is typically initiated by the inhalation of infectious particles which are able to reach the terminal pathways in lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages which travel to local lymph nodes, as well as into the blood stream and other tissues such as the bone marrow, spleen, kidneys, bone and central nervous system. (See Murray et al. *Medical Microbiology*, The C. V. Mosby Company 219-230 (1990)).

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

The interrelationship of colony morphology and virulence is particularly pronounced in *M. avium. M. avium* bacilli occur in several distinct colony forms. Bacilli which grow as transparent, or rough, colonies on conventional laboratory media are multiplicable within macrophages in tissue culture, are virulent when injected into susceptible mice, and are resistant to antibiotics. Rough or transparent bacilli, which are maintained on laboratory culture media, often spontaneously assume an opaque R colony morphology, at which time they are not multiplicable in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms which acts as a protective capsule. This capsule, or coating, is composed primarily of C-mycosides which apparently shield the virulent *M. avium* organisms from lysosomal enzymes and antibiotics. By contrast, the non-virulent opaque forms of *M. avium* have very little C-mycoside on their surface. Both the resistance to antibiotics and the resistance to killing by macrophages have been attributed to the glycolipid barrier on the surface of *M. avium*.

Diagnosis of mycobacterial infection is confirmed by the isolation and identification of the pathogen, although conventional diagnosis is based on sputum smears, chest X-ray examination (CXR), and clinical symptoms. Isolation of mycobacteria on a medium takes as long as four to eight weeks. Species identification takes a further two weeks. There are several other techniques for detecting mycobacteria such as the polymerase chain reaction (PCR), mycobacterium tuberculosis direct test, or amplified mycobacterium tuberculosis direct test (MTD), and detection assays that utilize radioactive labels.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multiprong inoculator (Tine test). Several problems exist with the skin test diagnosis method. For example, the Tine test is not generally recommended because the amount of antigen injected into the intradermal layer cannot be accurately controlled. (See Murray et al. *Medical Microbiology*, The C. V. Mosby Company 219-230 (1990)).

Although the tuberculin skin tests are widely used, they typically require two to three days to generate results, and many times, the results are inaccurate since false positives are sometimes seen in subjects who have been exposed to mycobacteria, but are healthy. In addition, instances of mis-diagnosis are frequent since a positive result is observed not only in active TB patients, but also in persons vaccinated with Bacille Calmette-Guerin (BCG), and those who had been infected with mycobacteria, but have not developed the disease. It is hard therefore, to distinguish active TB patients from the others, such as household TB contacts, by the tuberculin skin test. Additionally, the tuberculin test often produces a cross-reaction in those individuals who were infected with mycobacteria other than *M. tuberculosis* (MOTT). Therefore, diagnosis using the skin tests currently available is frequently subject to error and inaccuracies.

The standard treatment for tuberculosis caused by drug-sensitive organisms is a six-month regimen consisting of four drugs given for two months, followed by two drugs given for four months. The two most important drugs, given throughout the six-month course of therapy, are isoniazid and rifampin. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high. A variety of forms of patient-centered care are used to promote adherence with therapy. The most effective way of ensuring that patients are taking their medication is to use directly observed therapy, which involves having a member of the health care team observe the patient take each dose of each drug. Directly observed therapy can be provided in the clinic, the patient's residence, or any mutually agreed upon site. Nearly all patients who have tuberculosis caused by drug-sensitive organisms, and who complete therapy will be cured, and the risk of relapse is very low ("Ending Neglect: The Elimination of Tuberculosis in the United States" ed. L. Geiter Committee on the Elimination of Tuberculosis in the United States Division of Health Promotion and Disease Prevention, Institute of Medicine. Unpublished.)

What is needed are effective therapeutic regimens that include improved vaccination and treatment protocols. Currently available therapeutics are no longer consistently effective as a result of the problems with treatment compliance, and these compliance problems contribute to the development of drug resistant mycobacterial strains.

Ethambutol (EMB) is a widely used antibiotic for the treatment of TB, with over 300 million doses delivered for tuberculosis therapy in 1988.

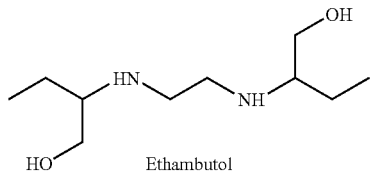

Ethambutol

Ethambutol, developed by Lederle Laboratories in the 1950s, has low toxicity and is a good pharmacokinetic. However, ethambutol has a relatively high Minimum Inhibition Concentration (MIC) of about 5 μg/ml, and can cause optic neuritis. Thus, there is an increasing need for new, and more effective, therapeutic compositions (See for example, U.S. Pat. Nos. 3,176,040, 4,262,122; 4,006,234; 3,931,157; 3,931,152; U.S. Re. 29,358; and Häusler et al., Bioorganic & Medicinal Chemistry Letters 11 (2001) 1679-1681). In the decoder years since the discovery of the beneficial effects of ethambutol, few pharmacological advances in TB treatment have been developed. Moreover, with the combined emergence of drug resistant strains, and the more prevalent spread of mycobacterial disease, it is becoming seriously apparent that new therapeutic compositions are crucial in the fight against tuberculosis.

Clearly effective therapeutic regimens that include improved vaccination and treatment protocols are needed. A therapeutic vaccine that would prevent the onset of tuberculosis, and therefore eliminate the need for therapy is desirable. Although currently available therapeutics such as ethambutol are effective, the emergence of drug resistant strains has necessitated new formulations and compositions that are more versatile than ethambutol. Currently available therapeutics are no longer consistently effective as a result of the problems with treatment compliance, lending to the development of drug resistant mycobacterial strains. What is needed are new anti-tubercular drugs that provide highly effective treatment, and shorten or simplify tuberculosis chemotherapy.

SUMMARY OF THE INVENTION

The present invention comprises methods and compositions comprising ethylene diamine compounds effective for the treatment of infectious disease. The present invention also provides methods and compositions comprising substituted ethylene diamines having improved anti-mycobacterial activity, including substituted ethylene diamines having improved anti-tuberculosis activity.

The present invention contemplates substituted ethylene diamines, which can derive from a variety of amine compounds. In the present invention, the substituted ethylene diamines are based on the following structure.

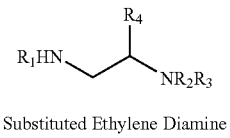

Substituted Ethylene Diamine

The substituted ethylene diamine compounds described herein are synthesized and screened for activity as follows. A chemical library of substituted ethylene diamines is prepared on a solid polystyrene support using split and pool technologies. This technique allows for the synthesis of a diverse set of substituted ethylene diamines. These diamines are screened for anti-TB activity using in vitro, biological assays, including a High-Throughput Screening (HTS) assay, based on the recently completed genomic sequence of *M. tuberculosis*, and a Minimum Inhibition Concentration (MIC) assay.

Figure 6:
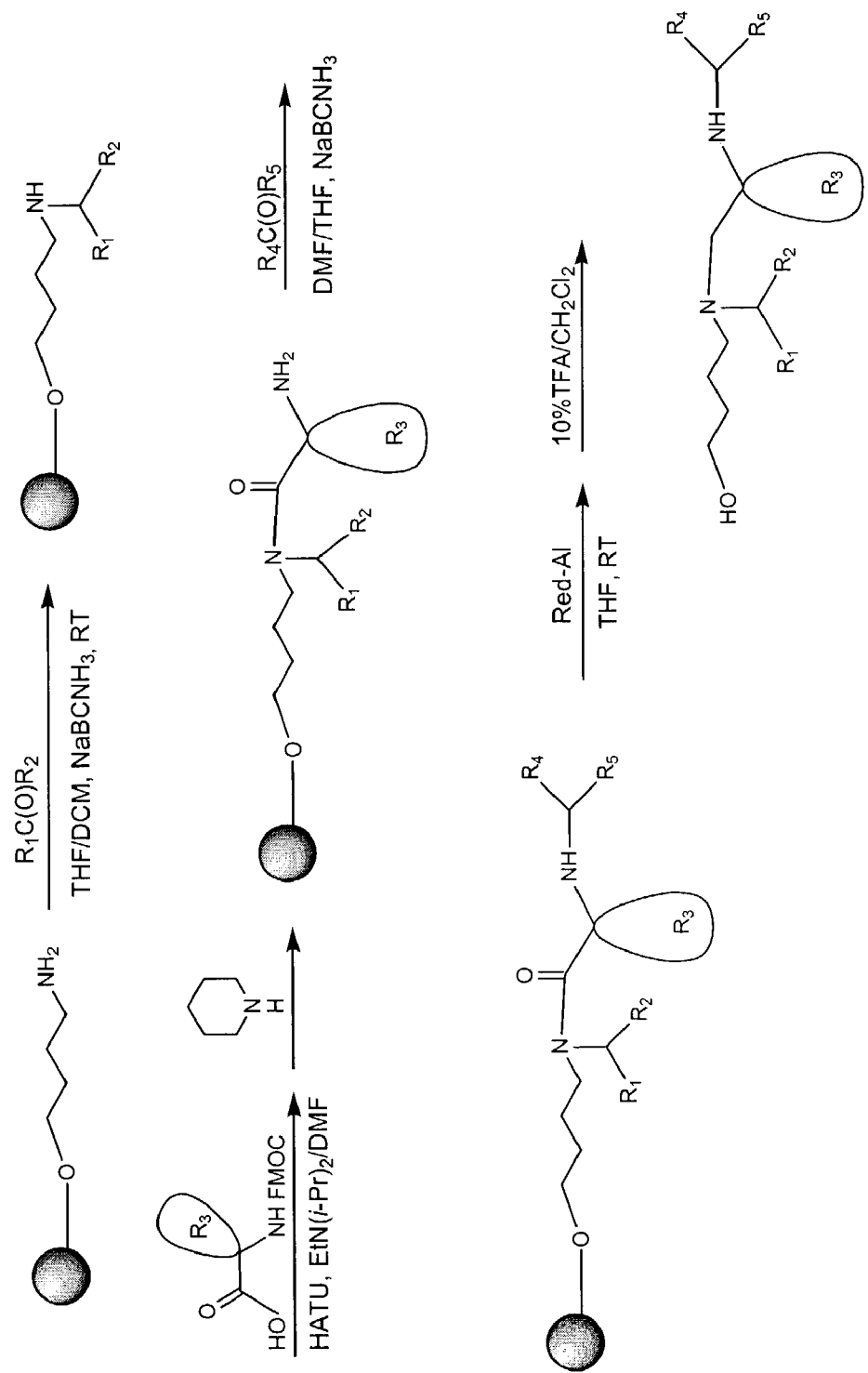

The methods and compositions described herein comprise substituted ethylene diamines that are effective against disease caused by infectious organisms, including, but not limited to, bacteria and viruses.

One embodiment of the invention provides methods and compositions comprising substituted ethylene diamines that are effective against mycobacterial disease.

Another embodiment of the invention provides methods and compositions comprising substituted ethylene diamines that have MIC of 50 μM or lower for mycobacterial disease.

Another embodiment of the present invention comprises substituted ethylene diamines that have an MIC of 25 μM or lower for mycobacterial disease. Yet another embodiment of the present invention comprises substituted ethylene diamines that have an MIC of 12.5 μM or lower for mycobacterial disease. Another embodiment of the present invention comprises substituted ethylene diamines that have an MIC of 5 μM or lower for mycobacterial disease. In another embodiment of the present invention, the methods and compositions comprise substituted ethylene diamines with HTS Luc activity of 10% or greater.

In yet another embodiment of the present invention, the methods and compositions comprise substituted ethylene diamines, wherein one amine group is derived from a primary amine, and wherein the other amine group is derived from a primary or secondary amine.

The present invention contemplates various salt complexes and other substituted derivatives of the substituted ethylene diamines. The present invention also contemplates enantiomers and other stereoisomers of the substituted ethylene diamines and their substituted derivatives. The present invention further contemplates treatment for animals, including, but not limited to, humans.

Accordingly, it is an object of the present invention to provide methods and compositions for the treatment and prevention of diseases caused by infectious agents.

Accordingly, it is an object of the present invention to provide methods and compositions for the treatment and prevention of infectious diseases.

Another object of the present invention is to provide methods and compositions for the treatment and prevention of mycobacterial disease, including but not limited to, tuberculosis.

Yet another object of the present invention is to provide methods and compositions for the treatment and prevention of infectious diseases using compositions comprising substituted ethylene diamines.

Another object of the present invention is to provide methods and compositions for the treatment and prevention of mycobacterial disease using compositions comprising substituted ethylene diamines.

Still another object of the present invention is to provide methods and compositions for the treatment and prevention of tuberculosis using compositions comprising substituted ethylene diamines.

Another object of the present invention is to provide methods and compositions for the treatment and prevention of tuberculosis using compositions comprising substituted ethylene diamines, wherein the diamine has an MIC of 50 μM, or less.

Another object of the present invention is to provide methods and compositions for the treatment and prevention of tuberculosis using compositions comprising substituted ethylene diamines, wherein the diamine has an MIC of 25 μM, or less.

Another object of the present invention is to provide methods and compositions for the treatment and prevention of tuberculosis using compositions comprising substituted ethylene diamines, wherein the diamine has an MIC of 12.5 μM, or less.

Yet another object of the present invention is to provide methods and compositions for the treatment and prevention of tuberculosis using compositions comprising substituted ethylene diamines, wherein the diamine has an MIC of 5 μM, or less.

Yet another object of the present invention is to provide methods and compositions for the treatment and prevention of tuberculosis using compositions comprising substituted ethylene diamines, wherein the diamine has HTS/Luc activity of 10% or greater.

Yet another object of the present invention is to provide composition for the therapeutic formulation for the treatment and prevention of mycobacterial disease.

Another object of the present invention is to provide compositions for therapeutic formulations for the treatment and prevention of mycobacterial disease caused by mycobacterial species comprising *M. tuberculosis* complex, *M. avium intracellulare, M. kansarii, M. fortuitum, M. chelonoe, M. leprae, M. africanum, M. microti, M. avium paratuberculosis*, or *M. bovis*.

These and other objects, features and advantages of the present invention will become apparent after a review of the following detailed description of the disclosed embodiments and the appended claims.

BRIEF DESCRIPTION OF THE FIGURES

FIG. 1 provides representative examples of diamine products synthesized from amino alcohol pre-loaded resins.

FIG. 2 provides commercially available amino alcohol pre-loaded resins.

FIG. 3 provides Table 1 which shows the prepared library of targeted 21,120 ethambutol analogs.

FIG. 4 provides Scheme 1, a schematic showing the Synthesis of the original 100,000 compound library of Ethambutol analogs.

FIG. 5 provides Scheme 2, a schematic showing the use of amino alcohol pre-loaded resins and amino acids as linker.

FIG. 6 provides Scheme 3, a schematic showing further modification of the linker: working with amino alcohol pre-loaded resins.

FIG. 7 provides Table 2 which lists the Amino acids used in the library preparation.

Figure 8:
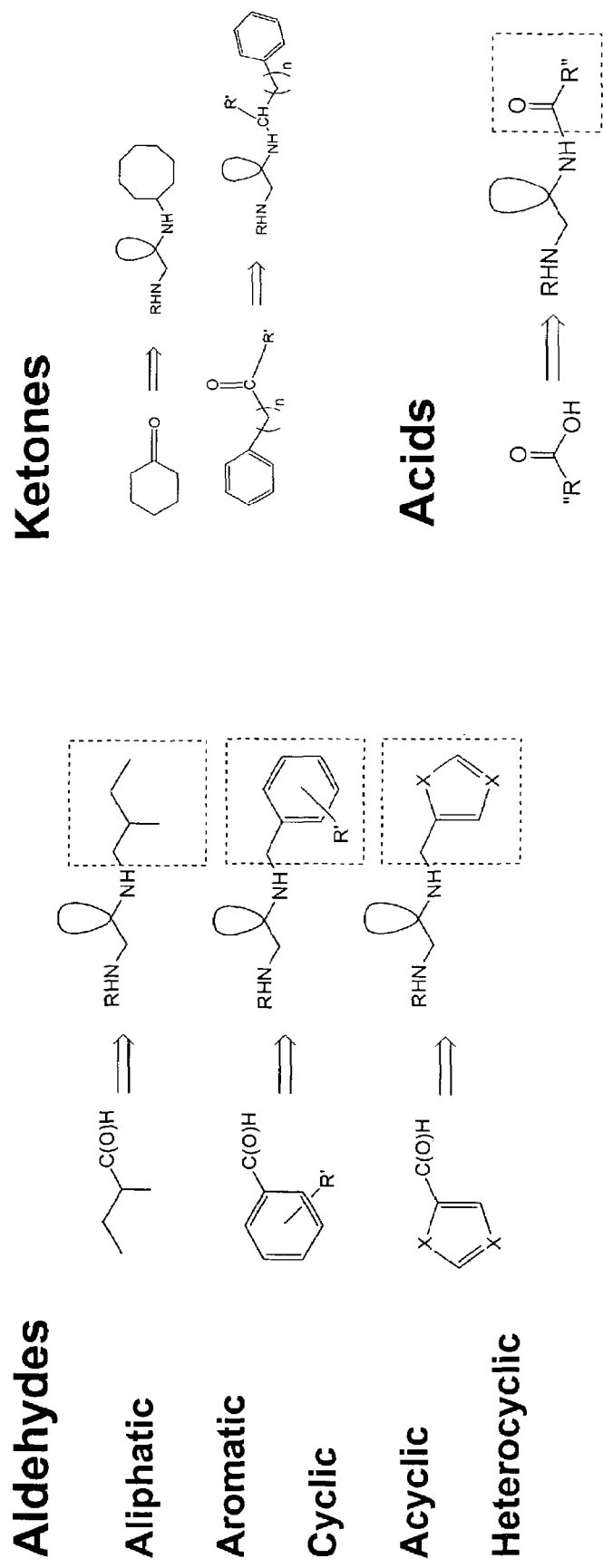

FIG. 8 provides representative carbonyl compounds used as reagents in the syntheses.

Figure 9:
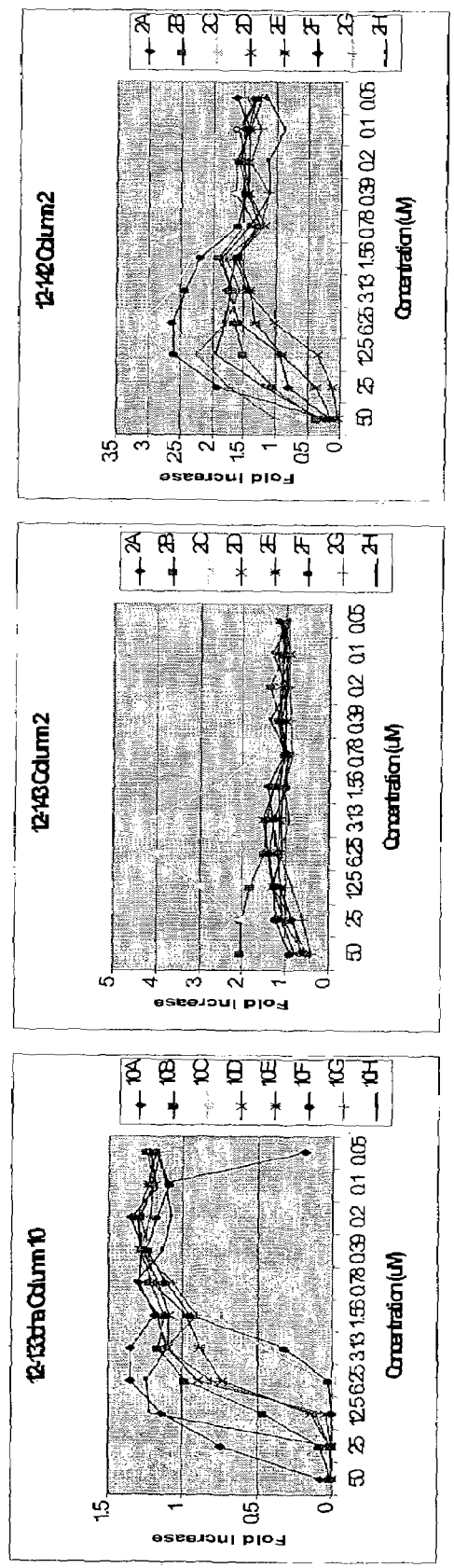

FIG. 9 provides representative examples of MIC and Lux data.

bacteria. Effective compositions and vaccines that target various strains of mycobacteria are necessary to bring the increasing number of tuberculosis cases under control.

Chemotherapy is a standard treatment for tuberculosis. Some current chemotherapy treatments require the use of three or four drugs, in combination, administered daily for two months, or administered biweekly for four to twelve months. Table 1 lists several treatment schedules for standard tuberculosis drug regimens.

TABLE 1

Treatment Schedules for Standard TB Drug Regimens.

| STANDARD DRUG REGIMEN | INDUCTION PHASE Dosing Schedule | DURATION | DRUG | CONTINUATION PHASE Dosing Schedule | DURATION |
| --- | --- | --- | --- | --- | --- |
| Isoniazid | Daily, DOT | 8 weeks | Isoniazid | 2/week, DOT | 16 weeks |
| Rifampicin | Daily, DOT | 8 weeks | Rifampicn | 2/week, DOT | 16 weeks |
| Pyrazinamide | Daily, DOT | 8 weeks | | | |
| Ethambutol or Streptomycin | Daily, DOT | 8 weeks | | | |

Figure 10:
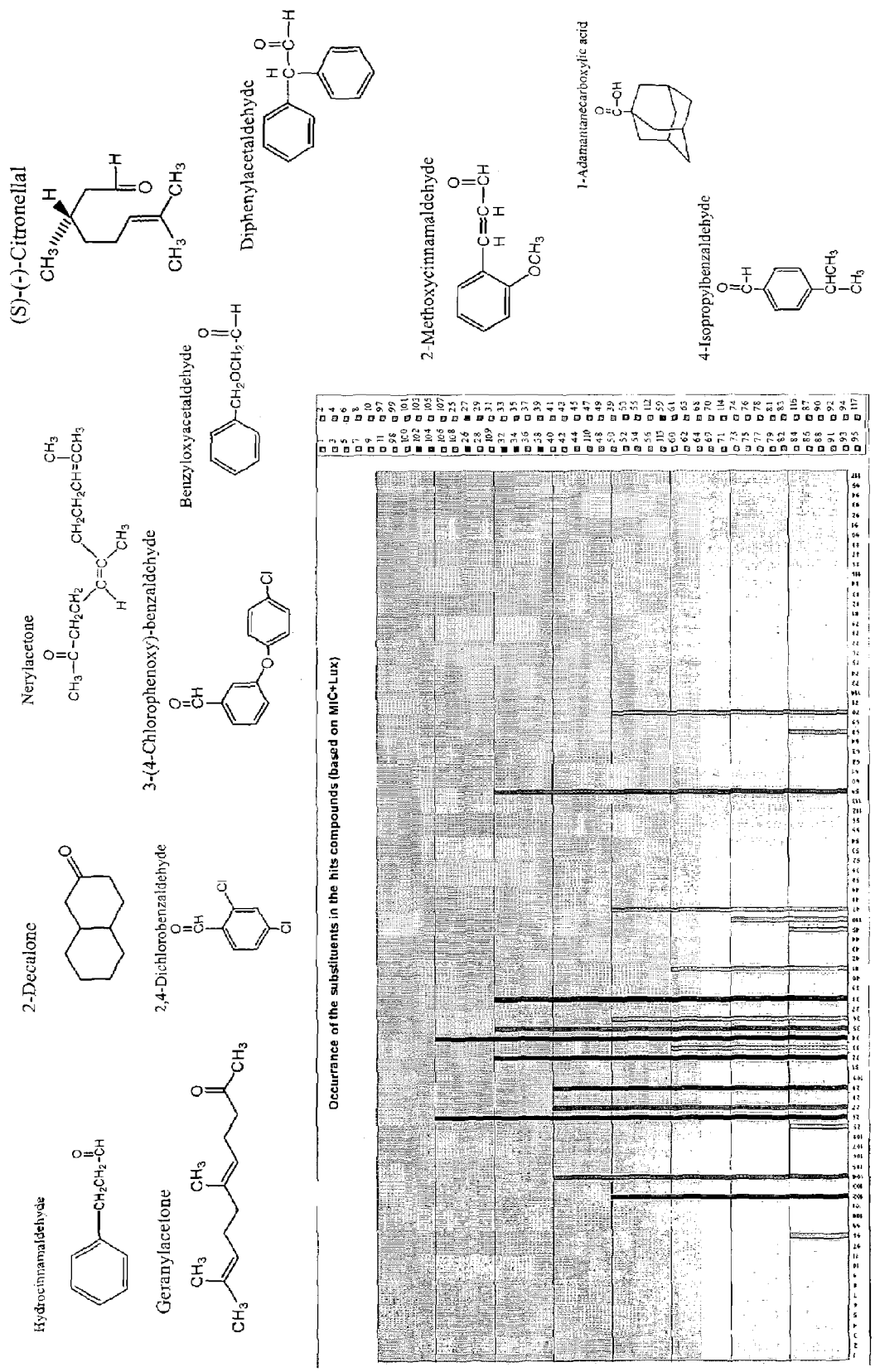

FIG. 10 shows the occurrence of alkylating monomers in the active molecules.

FIG. 11 provides a list of hit compounds and their structures.

FIG. 12 provides Table 3 which shows the layout for deconvolutions.

DETAILED DESCRIPTION

The present invention may be understood more readily by reference to the following detailed description of the specific embodiments included herein. However, although the present invention has been described with reference to specific details of certain embodiments thereof, it is not intended that such details should be regarded as limitations upon the scope of the invention. The entire text of the references mentioned herein are hereby incorporated in their entireties by reference including U.S. Provisional Patent Application Serial No. 60/381,244 filed May 17, 2002 and U.S. patent application Ser. No. 10/147,587 filed May 17, 2002.

Mycobacterial infections, such as those causing tuberculosis, once thought to be declining in occurrence, have rebounded, and again constitute a serious health threat. Tuberculosis (TB) is the cause of the largest number of human deaths attributed to a single etiologic agent with two to three million people infected with tuberculosis dying each year. Areas where humans are crowded together, or living in substandard housing, are increasingly found to have persons affected with mycobacteria. Individuals who are immuno-compromised are at great risk of being infected with mycobacteria and dying from such infection. In addition, the emergence of drug-resistant strains of mycobacteria has led to treatment problems of such infected persons.

Many people who are infected with mycobacteria are poor, or live in areas with inadequate healthcare facilities. As a result of various obstacles (economical, education levels, etc.), many of these individuals are unable to comply with the prescribed therapeutic regimens. Ultimately, persistent non-compliance by these and other individuals results in the prevalence of disease. This noncompliance is frequently compounded by the emergence of drug-resistant strains of myco- Decades of misuse of existing antibiotics and poor compliance with prolong and complex therapeutic regimens has led to mutations of the *mycobacterium tuberculosis* and has created an epidemic of drug resistance that threatens tuberculosis control world wide. The vast majority of currently prescribed drugs, including the front line drugs, such as isoniazid, rifampin, pyrazinamide, ethambutol and streptomycin were developed from the 1950s to the 1970s. Thus, this earlier development of tuberculosis chemotherapy did not have at its disposal the implications of the genome sequence of *Mycobacterium tuberculosis*, the revolution in pharmaceutical drug discovery of the last decades, and the use of national drug testing and combinational chemistry.

Consequently, the treatments of drug-resistant *M. tuberculosis* strains, and latent tuberculosis infections, require new anti-tuberculosis drugs that provide highly effective treatments, and shortened and simplified tuberculosis chemotherapies. Moreover, it is desirable that these drugs be prepared by a low-cost synthesis, since the demographics of the disease dictate that cost is a significant factor.

The present invention provides methods and compositions comprising a class of substituted ethylene diamine compounds effective in treatment and prevention of disease caused by microorganisms including, but not limited to, bacteria. In particular, the methods and compositions of the present invention are effective in inhibiting the growth of the microorganism, *M. tuberculosis*. The methods and compositions of the present invention are intended for the treatment of mycobacteria infections in human, as well as other animals. For example, the present invention may be particularly useful for the treatment of cows infected by *M. bovis*.

As used herein, the term "tuberculosis" comprises disease states usually associated with infections caused by mycobacteria species comprising *M. tuberculosis* complex. The term "tuberculosis" is also associated with mycobacterial infections caused by mycobacteria other than *M. tuberculosis* (MOTT). Other mycobacterial species include *M. avium-intracellulare*, *M. kansarii*, *M. fortuitum*, *M. chelonae*, *M. leprae*, *M. africanum*, and *M. microti*, *M. avium paratuberculosis*, *M. intracellulare*, *M. scrofulaceum*, *M. xenopi*, *M. marinum*, *M. ulcerans*.

The present invention further comprises methods and compositions effective for the treatment of infectious disease, including but not limited to those caused by bacterial, mycological, parasitic, and viral agents. Examples of such infectious agents include the following: staphylococcus, streptococcaceae, neisseriaaceae, cocci, enterobacteriaceae, pseudomonadaceae, vibrionaceae, campylobacter, pasteurellaceae, bordetella, francisella, brucella, legionellaceae, bacteroidaceae, gram-negative bacilli, clostridium, corynebacterium, propionibacterium, gram-positive bacilli, anthrax, actinomyces, nocardia, mycobacterium, treponema, borrelia, leptospira, mycoplasma, ureaplasma, rickettsia, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picomaviruses, reoviruses, togaviruses, flaviviruses, bunyaviridae, rhabdoviruses, human immunodeficiency virus and retroviruses.

The present invention further provides methods and compositions useful for the treatment of infectious disease, including by not limited to, tuberculosis, leprosy, Crohn's Disease, aquired immunodeficiency syndrome, lyme disease, cat-scratch disease, Rocky Mountain Spotted Fever and influenza.

Second Generation Antibiotics from Ethambutol

The present invention is particularly directed to a novel library of diamine compounds of Ethambutol family comprising a modified ethylene linker starting from commercially available amino alcohol pre-loaded resins.

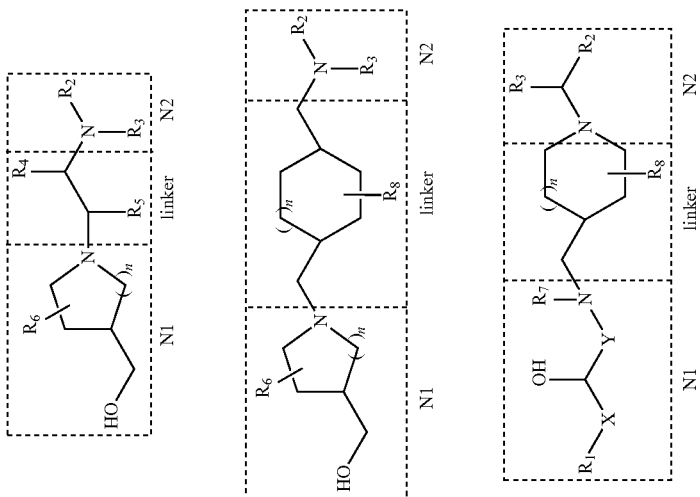
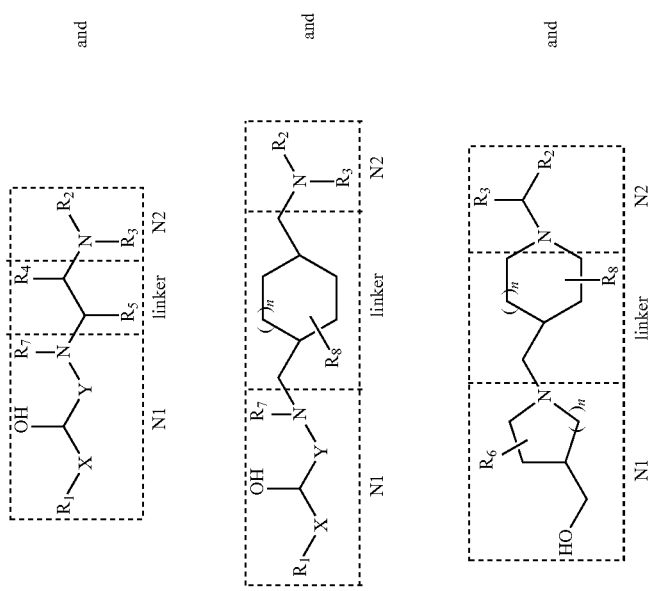
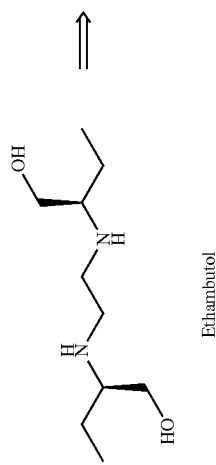

In an effort to enhance the structural diversity of our library of Ethambutol analogs and to assess the influence of a modified linker on the activity of structurally diverse diamines against M. tuberculosis, the synthetic scheme to incorporate amino acids into the bridging linker between the two amine components was modified. Use of amino acids was of a special interest since it allowed introduction of another diversity element into the linker (as R4), as well as chirality.

It was crucial for the project to synthesize a sub-library of diamines closely related to Ethambutol by having amino alcohol moiety in the molecule, and yet quite different due to presence an elaborate linker between the two amine atoms (see FIG. 1 for representative examples). Also, the fact that the 2-Chlorotrityl resins with pre-loaded amino alcohols are commercially available (FIG. 2) and suit well proposed chemistry was very attractive.

The compounds in the library were prepared on mmol scale in 96-well format in pools of 10 compounds per well (for the vast majority of the plates). Table 1 (FIG. 3) summarizes data for the synthesized plates.

Solid phase syntheses using amino alcohol pre-loaded resins. Twenty 96-well plates have been prepared. Four- and five-steps synthetic routes starting from commercially available amino alcohol pre-loaded resins similar to what had been used to create our first 100,000 compound library (Scheme 1, FIG. 4), were applied to make targeted diamines (Schemes 2 and 3, FIGS. 5 and 6 respectively). There are some differences in the syntheses: (1) two first steps of the Scheme 1 are abandoned in Schemes 2 and 3; (2) in the Scheme 1, the second amine is introduced into the molecule as a whole synthon via nucleophilic displacement of Cl-function of the linker, while in the Schemes 2 and 3, it proceeds through modification of the existing amino moiety by carbonyl compounds.

Scheme 2. Acylation of the purchased amino alcohol pre-loaded 2-Chlorotrityl resins was accomplished via peptide coupling with FMOC protected amino acids in presence of HATU (O-(7-Azabenzotriazol-1-yl)-N,N,N,N-tetramethyluronium hexafluorophosphate) and $EtN(iso\text{-}Pr)_2$ in DCM/DMF mixture at RT. The reaction was done twice to improve product yields. The list of the amino acids used to create this library is shown in the Table 2 (FIG. 7).

Deprotection (removal of the FMOC group) was carried out by reaction with piperidine at RT. Derivatization of the amino group was achieved by reductive alkylation with 96 various carbonyl compounds, such as aldehydes, ketones, and carboxylic acids, in the presence of $NaBCNH_3$ at RT for 72-96 h. The selection of the carbonyl compounds was made so, that the final diamine products would carry the same or similar types of substituents that had been observed in the hit compounds generated from the previous library of ethambutol analogs, as well as structural diversity (FIG. 8). A complete list of the carbonyl compounds used is shown in Table 3 (FIG. 8).

Reduction of the aminoethyleneamides into corresponding diamines was carried out using the soluble reducing reagent 65+w % Red-Al at room temperature. Cleavage of the products from the resin was achieved with a 10% solution of trifluoroacetic acid in dichloromethane resulting in the formation of TFA salts of the diamines.

For library production the acylation step of the synthetic scheme was carried out using a Quest 210 Synthesizer on scale of 0.1-0.15 g of resin per tube. Following the reaction, formed resins were thoroughly washed, dried, and then groups of ten resins were pooled together. A small amount of each resin (~0.05 g) was archived prior to pooling to facilitate re-synthesis and deconvolution of actives.

Deprotection of the FMOC group, addition of the carbonyl component, reduction, and cleavage were carried out in 96-well reaction blocks using the Combiclamps system by Whatman Polyfiltronics or the FlexChem system by Robbins Scientific. A suspension of the pooled resins in 2:1 mixture of DCM/THF was evenly distributed into one reaction plate resulting in approximately 10 mg of the resin per well. The 96 diverse carbonyl compounds were arrayed in one 96-well plate template and added, one carbonyl compound per well, to each individual pool of ten resins, resulting in an anticipated 960 diamines produced per plate. Reduction was carried out in the same format and cleavage and filtering into storage plates was followed by evaporation of the TFA prior to biological assay.

Quality assessment of the prepared library of diamines was done by Electrospray Ionization mass spectrometry using two randomly selected rows (16 samples) per plate, 17% of the total number. Successful production of a compound was based on an appearance of a molecular ion of the calculated mass. Depending on the amino acid that had been used for the synthesis, the percentage of the predicted ions were observed and therefore the predicted compounds were formed, varied from 31-96% (Table 1, FIG. 3). Based on MS analysis, out of targeted 15,360 compounds, 7,500 diamines were actually formed. Amino acids such as aminomethylcylcohexyl carboxylic acid, thienylalanine, or phenylalanine produced desirable compounds with good yields (88-96%). At the same time, some amino acids, such as arginine, tetrahydroisoquinoline carboxylic acid, and thiazolidine carboxylic acid did not lead to the corresponding products.

Scheme 3. Success in preparation of ethambutol analogs with modified linker encouraged us to attempt synthesis of another sub-library of diamines using commercially available amino-alcohol pre-loaded resins (Scheme 3, FIG. 6). This route yields diamine compounds that are similar to those produced by the (Scheme 2, FIG. 5) but that also possess desirable substituents at the first nitrogen atom.

We have illustrated this method by starting from commercially available 1,4-aminobutanol pre-loaded resin. We prepared five plates using five amino acids Phe, Amc, Cha, Trp, and Inp (Table 1) that gave the best preliminary results in the screening assays (see number of hits in the Table 1). The very first step was derivatization of the amino group via reductive alkylation by 10 carbonyl compounds (cyclooctanone, 4-benzyloxybenzaldehyde, (S)-citronellal, myrtenal, tetrahydro-4H-pyran-4-one, norcamphor, 4-(4-hydroxyphenyl)2-butanone, geranylacetone, 2-decalone, 2-adamantanone) in presence of $NaBCNH_3$ at RT. The following steps were carried out in a similar fashion as we reported earlier for the Scheme 2.

Screening the library against *M. tuberculosis* and deconvolution of the active mixtures. A high-throughput assay with recombinant mycobacteria containing a promoter fusion of luciferase to Rv0341, as well as the MICs, has been used to screen this new compound library of ethambutol analogs, FIG. 9.

198 compound mixtures have shown to exhibit anti-TB activity, Table 1 (activity at <12.5 uM in the HTS Luc assay and/or with an MIC of <12.5 uM), have been selected for deconvolutions. Deconvolutions of all 198 compound mixtures were performed by the discrete re-synthesis of the diamine compounds in 96-well format using stored archive resins (prior pooling them together) and the same synthetic Schemes 2 and 3. The same screening tests were used for every deconvoluted plate. Few carbonyl compounds have been identified as potent synthons contributing to the anti-TB activity (FIG. 5). Performed deconvolutions revealed 118 hits of novel structures as potent anti-TB compounds (Table 4), 38 of those compounds were proven to be active in both assays. FIG. 11 provides a list of hit compounds and their structures.

Formulations

Therapeutics, including compositions containing the substituted ethylene diamine compounds of the present invention, can be prepared in physiologically acceptable formulations, such as in pharmaceutically acceptable carriers, using known techniques. For example, a substituted ethylene diamine compound is combined with a pharmaceutically acceptable excipient to form a therapeutic composition.

The compositions of the present invention may be administered in the form of a solid, liquid or aerosol. Examples of solid compositions include pills, creams, soaps and implantable dosage units. Pills may be administered orally. Therapeutic creams and anti-mycobacteria soaps may be administered topically. Implantable dosage units may be administered locally, for example, in the lungs, or may be implanted for systematic release of the therapeutic composition, for example, subcutaneously. Examples of liquid compositions include formulations adapted for injection intramuscularly, subcutaneously, intravenously, intraarterially, and formulations for topical and intraocular administration. Examples of aerosol formulations include inhaler formulations for administration to the lungs.

A sustained release matrix, as used herein, is a matrix made of materials, usually polymers, which are degradable by enzymatic or acid/base hydrolysis, or by dissolution. Once inserted into the body, the matrix is acted upon by enzymes and body fluids. The sustained release matrix is chosen desirably from biocompatible materials, including, but not limited to, liposomes, polylactides, polyglycolide (polymer of glycolic acid), polylactide co-glycolide (coplymers of lactic acid and glycolic acid), polyanhydrides, poly(ortho)esters, polypeptides, hyaluronic acid, collagen, chondroitin sulfate, carboxylic acids, fatty acids, phospholipds, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide.

The dosage of the composition will depend on the condition being treated, the particular composition used, and other clinical factors, such as weight and condition of the patient, and the route of administration. A suitable dosage may range from 100 to 0.1 mg/kg. A more preferred dosage may range from 50 to 0.2 mg/kg. A more preferred dosage may range from 25 to 0.5 mg/kg. Tablets or other forms of media may contain from 1 to 1000 mg of the substituted ethylene diamine. Dosage ranges and schedules of administration similar to ethambutol or other anti-tuberculosis drugs may be used.

The composition may be administered in combination with other compositions and procedures for the treatment of other disorders occurring in combination with mycobacterial disease. For example, tuberculosis frequently occurs as a secondary complication associated with acquired immunodeficiency syndrome (AIDS). Patients undergoing AIDS treatment, which includes procedures such as surgery, radiation or chemotherapy, may benefit from the therapeutic methods and compositions described herein.

The following specific examples will illustrate the invention as it applies to the particular synthesis of the substituted ethylene diamine compounds, and the in vitro and in vivo suppression of the growth of colonies of *M. tuberculosis*. In addition, the teachings of R. Lee et al. J. Comb. Chem 2003, 5, 172-187 are hereby incorporated by reference in their entirety. It will be appreciated that other examples, including minor variations in chemical procedures, will be apparent to those skilled in the art, and that the invention is not limited to these specific illustrated examples.

EXAMPLE I

Generating the Diamine Library from Commercially Available Amino Alcohol Pre-Loaded Resins General Methods: All reagents were purchased from Sigma-Aldrich. Amino alcohol pre-loaded resins were purchased from NovaBiochem. Solvents acetonitrile, dichloromethane, dimethylformamide, ethylene dichloride, methanol, and tetrahydrofuran were purchased from Aldrich and used as received. Solid phase syntheses were performed on Quest 210 Synthesizer (Argonaut Technologies) and combinatorial chemistry equipment (Whatman Polyfiltronics and Robbins Scientific). Evaporation of the solvents was done using SpeedVac AES (Savant). Mass spectra data were obtained by Electrospray Ionization technique on Perkin Elmer/Sciex, API-300, TQMS with an autosampler.

Scheme 2. Description of the Process.

The acylation step was carried out in 5 ml tubes using the Quest 210 Synthesizer. Removal of the FMOC group, reductive alkylation reaction with carbonyl compounds, the reduction with Red-Al, and the cleavage from the solid support were carried out in 96-deep (2 ml) well, chemically resistant plates.

Step 1. Acylation of Amino Alcohol Pre-Loaded Resins with Amino Acids.

Each tube was loaded 0.150 g of corresponding resin (coverage of 0.3-1.0 mmol/g), and all resins were pre-swollen in DCM for 1.5 h and filtered. If Fmoc protected resin was used: the resin was stirred with 2.5 ml of 20% solution of piperidine in DMF for 10 min, filtered, and washed with 2.5 ml of DMF. The procedure was repeated, but the stirring time was 20 min. After that all resins were filtered, washed with DMF (1×2.5 ml) and DCM (2×3 ml). Each tube was charged with 1 ml of dichloromethane. Amino acids, 0.38 mmol in 1 ml of DMF (2,5 mol excess to loaded resin) were mixed with HATU, 0.3 mmol, 011 g in 0.5 ml of DMF (2 mol excess to loaded resin) and allowed to stay for 15-20 min. Then 1.5 ml of mixture acid-HATU were added to each tube following by the addition of solution of 1.5 mmol, 0.26 ml (10 mol excess to loaded resin) of $EtNiPr_2$ in 0.5 ml of dichloromethane. Reaction carried out 8 h at 45° C. and 6-8 h at room temperature. After the reaction was complete, the resins were filtered, washed with 1:1 mixture of DMF and dichloromethane (1×3 ml), dichloromethane (1×3 ml), and acylation was repeated with the same amount of reagents. At the end, the resins were filtered, washed with 1:1 mixture of DMF and dichloromethane (1×3 ml), methanol (3×3 ml), sucked dry (on Quest) for 30 min and transferred into vials (one resin per vial), and dried in a desiccator under vacuum for 1 h. After this step all resins were subjected for quality control using MS spectra.

Step 2. Alkylation of the Amino Group.

Deprotection. Ten prepared resins from the first three steps were pooled together, leaving approximately 0.03 g of each in the individual vials for all necessary deconvolutions. A suspension of the resin mixture (0.08-1.0 g) in 100 ml of a 2:1 mixture of dichloromethane and THF was distributed into two 96-well filterplates and filtered using a filtration manifold. The reaction plates were transferred into combiclamps, and 0.2 ml of 20% solution of piperidine in DMF was added to remove Fmoc protecting group and allowed to stay for 10 min. After 10 min plate was filtered, washed with 0.2 ml of DMF, and deprotection was repeated with 0.2 ml of 20% solution of piperidine in DMF and allowed to stay for 20 min. After that plate was filtered, washed with DMF (0.2 ml per well) and dichloromethane (2×0.5 ml per well).

Reaction with the carbonyl compounds. Each well in row A on the reaction plate was charged with 0.1 ml of dichloromethane, 0.08 ml of ~1.0M solution of appropriate acid in DMF from master plate, 0.05 ml DMF solution of PyBrop, (0.012 g, 0.025 mmol, 2.5 mol excess to loaded resin) and 0.05 ml of EtNiPr$_2$ in dichloromethane (0.017 ml, 0.10 mmol, 10 mol excess to loaded resin). Each well in rows B through H was charged with 0.1 ml of THF, 0.160 ml of ~1.0 M solution of appropriate aldehyde or ketone in DMF from master plate and allowed to react for 30 min. After 30 min 0.075 ml (0.075 mmol) of 1.0 M solution of NaBCNH$_3$ in THF were added. The reaction plates were sealed and kept at RT for 72 h. At the end, the resins were filtered, washed with THF, DCM (1×1 ml), methanol (2×1 ml) and dried in desiccator under vacuum for 3 h.

Step 3. Reduction with Red-AL.

The reaction plates were placed into combiclamps. A 1:6 mixture of Red-Al (65+ w % in toluene) and THF was added, 0.6 ml per well (0.28 mmol of Red-Al per well), and allowed to react for 4 h. After the reaction completion the resins were filtered, washed with THF (2×1 ml), methanol (3×1 ml) and dried in the filtration manifold.

Step 4. Cleavage.

This step was carried out using a cleavage manifold. The reaction plates (placed on the top of the collection plates in this manifold) were charged with a 10:88:2 mixture of TFA, dichloromethane, and triisopropylsilane, 0.5 ml per well. After 15 min, the solutions were filtered and collected into proper wells of the collection plates. The procedure was repeated. Solvents were evaporated on a speedvac, and the residual samples were ready for testing.

Scheme 3. Description of the Process.

The reductive alkylation step of 4-aminobutan-1 ol resin and the acylation step were carried out in 5 ml tubes using the Quest 210 Synthesizer. Removal of the FMOC group, reductive alkylation reaction with carbonyl compounds, the reduction with Red-Al, and the cleavage from the solid support were carried out in 96-deep (2 ml) well, chemically resistant plates.

Step 1. Reductive Alkylation of 4-Aminobutan-1-ol Resin.

A suspension of the resin (coverage of 0.3-1.0 mmol/g), 1.0 g (up to 1.0 mmol), in 30 ml of 2:1 mixture of dichloromethane and THF was disitrubuted into 10 tubes, 3 ml per tube and filtered, than each tube was charged with 0.10 g of resin. Resin was pre swollen in DCM for 1.5 h and filtered. Each tube were loaded with 1.5 ml 1,2-dichloroethane, 0.3 mmol (3 mol excess) of corresponded aldehyde or ketone (alkylating reagent) and allowed to react for 30 min. After that 0.3 mmol (0.3 ml) of 1 M solution of NaBCNH$_3$ in THF were added and reaction was carried out at RT for 48 h. When reaction was completed, all tubes were filtered, washed with THF (2×3 ml), MeOH (3×3 ml) and sucked dry (on Quest for ~30 min).

Step 2. Acylation with Amino Acids.

All tubes were pre washed with DCM twice. Each tube was charged with 1 ml of dichloromethane. Amino acids, 0.25 mmol in 1 ml of DMF (2,5 mol excess to loaded resin) were mixed with HATU, 0.2 mmol, 0.076 g in 0.5 ml of DMF (2 mol excess to loaded resin) and allowed to stay for 15-20 min. Then 1.5 ml of mixture acid-HATU were added to each tube following by the addition of solution of 1.0 mmol, 0.17 ml (10 mol excess to loaded resin) of EtNiPr$_2$ in 0.5 ml of dichloromethane. Reaction carried out 8 h at 45° C. and 6-8 h at room temperature. After 16 h the resins were filtered, washed with 1:1 mixture of DMF and dichloromethane (1×3 ml), dichloromethane (1×3 ml) and acylation was repeated with the same amount of reagents. At the end, the resins were filtered, washed with 1:1 mixture of DMF and dichloromethane (1×3 ml), methanol (3×3 ml), sucked dry (on Quest) for 30 min and transferred into vials (one resin per vial), and dried in a desiccator under vacuum for 1 h. After this step all resins were subjected for quality control using MS spectra.

All following reaction steps,—alkylation of the amino group (Step 3), reduction with Red-Al (Step 4), and Cleavage (Step 5),—were carried as they were described for the Scheme 2 of this Application.

EXAMPLE 2

Deconvolution

Deconvolution of the active wells was performed by re-synthesis of discrete compounds, from the archived FMOC-protected-aminoacetamide resins (10 resins, 0.05-0.10 g each), which were set aside at the end of the acylation step before the pooling. Each resin was assigned a discrete column (1, or 2, or 3, etc.) in a 96-well filterplate, and was divided between X rows (A, B, C, etc), where X is the number of hits discovered in the original screening plate. To each well, in a row, a selected carbonyl compound (present in the hit) was added along with other required reagents: the first selected carbonyl compound was added to the resins in the row "A", the second carbonyl compound—to the resins in the row "B", the third carbonyl compound—to the resins in the row "C", etc. A lay-out of a representative 96-well deconvolution plate is shown in Table 3, FIG. 12.

The reaction plates were sealed and kept at RT for 72 h. At the end, the resins were filtered, washed with THF, DCM (1×1 ml), methanol (2×1 ml) and dried in desiccator under vacuum for 2 h. Reduction and cleavage were performed according to steps 5 and 6 of the synthetic protocol. The product wells from the cleavage were analyzed by ESI-MS (Electrospray Ionization Mass Spectroscopy) to ensure the identity of the actives, and were tested in the MIC assay.

Solid Phase Synthesis of Selected Substituted Ethylenediamines Using the Quest 210 Synthesizer.

The solid phase protocol described above for generating a library of diamine compounds was applied to the scale-up synthesis of the selected substituted ethylenediamine compounds. Here, all reaction steps, from the acylation of the commercially available amino alcohol pre-loaded resins to the cleavage of the final product, were carried out using Quest instrument only, which allowed for up to twenty parallel reactions. Purification of all crude samples was done by Flash Chromatography on CombiFlash (Isco, Inc.) to yield desirable products in purity greater than 90%. Here, the synthesis of one of the active compounds, 1-(2-{[3-(4-chlorophenoxy) benzyl]amino}-3-phenylpropyl)piperidin-4-ol, is described below as an example.

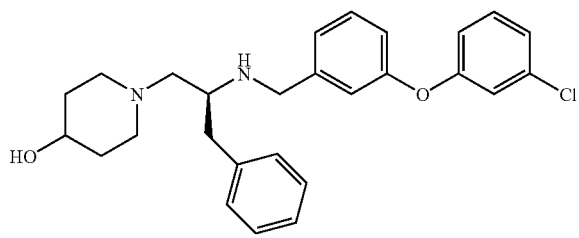

Compound 588

The preparation of 1-(2-{[3-(4-chlorophenoxy)benzyl]amino}-3-phenylproply)piperidin-4-ol, compound 588.

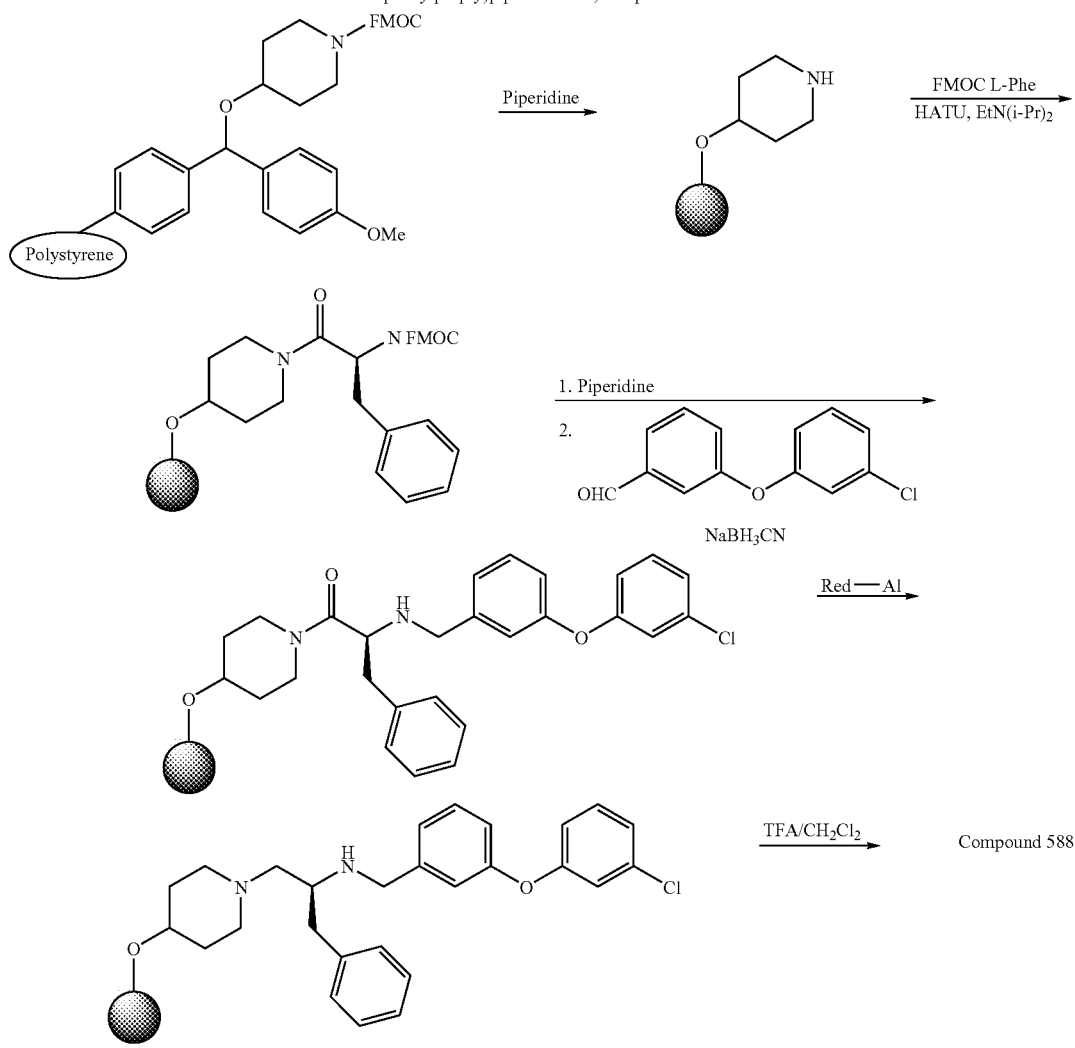

Representative Synthesis of Active Compounds.

Removal of FMOC protective group. Commercially available resin (N-FMOC-piperidinyl-4-oxy)-(4-methoxyphenyl) methyl polystyrene, coverage (linker) 0.88 mmol/g (0.4 g, 0.35 mmol), was placed into one of the 10 ml tubes of Quest 210 Synthesizer. A solution of piperidine (1.5 ml) in DMF (6 ml) was added and stirred for 30 min, filtered, washed with DMF (1×6 ml), and the addition of piperidine was repeated. The resin was washed with DMF (1×8 ml) and DCM (2×8 ml).

Acylation with FMOC protected L-Phenylalanine. The resin was pre-washed with 5 ml of DCM for 20 min. FMOC L-Phenylalanine, (0.0341 g, 0.88 mmol) in 1 ml of DMF (2,5 mol excess to loaded resin) were mixed with HATU (0.33 g, 0.88 mmol) in 3 ml of DMF, and added to the tube following by the addition of solution of 0.6 ml of EtNiPr$_2$. Reaction was carried at RT for 20 h. After the reaction was complete, the resin was filtered, washed with 1:1 mixture of DMF and dichloromethane (1×6 ml), dichloromethane (1×6 ml), and acylation was repeated with the same amount of reagents. At the end, the resins were filtered, washed with 1:1 mixture of DMF and dichloromethane (2×6 ml).

Removal of FMOC protective group. A solution of piperidine (1.5 ml) in DMF (6 ml) was added to the resin and formed suspension was stirred for 30 min, filtered, washed with DMF (1×6 ml), and the addition of piperidine was repeated. The resin was washed with DMF (1×8 ml) and methanol (2×8 ml), and sucked dry inder Ar for 20 min.

Reaction with a carbonyl compound. The resin was pre-washed with THF for 30 min, filtered, and charged with 6 ml of THF. 3-(4-Chlorophenoxy)-benzaldehyde (0.280 ml, 1.00 mmol) was added followed by addition of 1.0 M solution of NaBCNH$_3$ in THF (1 ml, 1 mmol) after 30 min. The reaction was allowed to proceed at RT for 72 h. At the end, the resin was filtered, washed with THF (1×6 ml) and MeOH (2×6 ml), and dried under Ar for 30 min.

Reduction with Red-Al. The resulted resin in a tube was pre-washed with anhydrous THF (2×6 ml) and filtered. The tube was charged with 5 ml of anhydrous THF followed by addition upon stirring commercially available Red-Al as 65+% in toluene (1 ml, 3.2 mmol). After 4 h the resin was filtered, washed with THF (2×1 ml) and MeOH (3×1 ml) (addition of MeOH should proceed with caution!), and dried under Ar for 10 min.

Cleavage. For this last step of the synthesis the tube with the resin was charged with DCM (8 ml) and TFA (1 ml) and formed bright red suspension was allowed to stir for 30 min. The resin was filtered and the filtrate was collected into a collection tube. The procedure was repeated. DCM and excess of TFA were evaporated on a speedvac. Crude 1-(2-{[3-(4-chlorophenoxy)benzyl]amino}-3-phenylpropyl)piperidin-4-ol (in a form of trufluoroacetate salt) was purified by Flash Chromatography on CombiFlash (Isco) using following conditions: pre-loaded silica gel column, 12 g, flow 15 m/min, 25 min run, gradient starting with DCM finishing up with DCM/MeOH/NH$_4$OH (600/400/10). Obtained: 0.128 mg of 1-(2-{[3-(4-chlorophenoxy)benzyl]amino}-3-phenylpropyl)piperidin-4-ol ditrifluoroacetate, 53% yield, of at least 95% purity. Mass spectrum (ESI) m/z (MH)$^+$ 451.2, 453.2.

We claim:

1. A compound selected from the group consisting of:

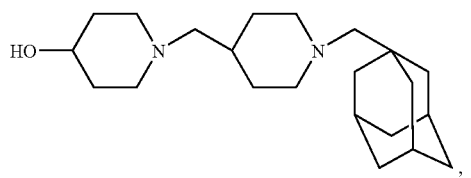

Compound 609

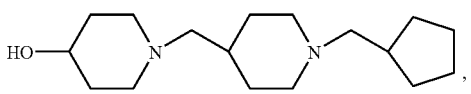

Compound 610

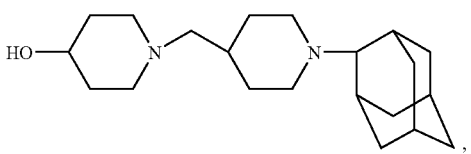

Compound 611

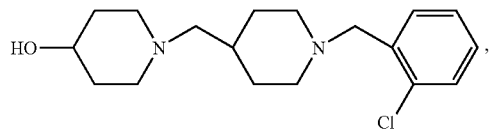

Compound 612

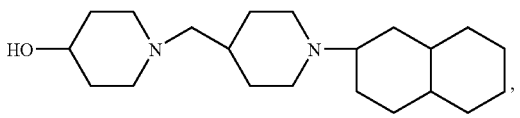

Compound 613

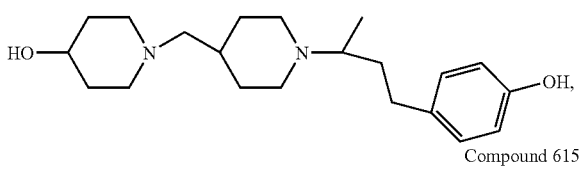

Compound 614

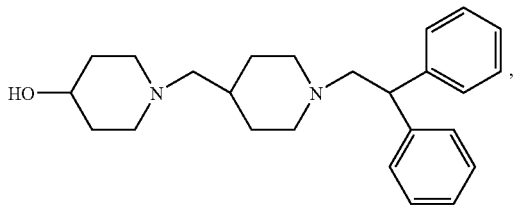

Compound 615

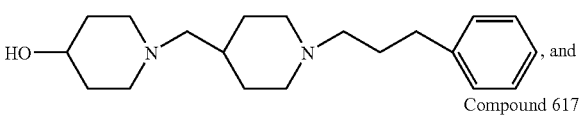

Compound 616

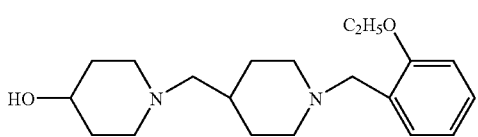

Compound 617 or a salt thereof.

2. A pharmaceutical composition comprising a compound of claim 1 and a pharmaceutically acceptable carrier.

3. The pharmaceutical composition of claim 2, wherein the composition is in the form of a solid.

4. The pharmaceutical composition of claim 3, wherein the composition is suitable for oral administration.

5. The pharmaceutical composition of claim 3, wherein the composition is suitable for topical administration.

6. The pharmaceutical composition of claim 2, wherein the composition is in the form of a liquid.

7. The pharmaceutical composition of claim 6, wherein the composition is suitable for intravenous administration.

8. The pharmaceutical composition of claim 6, wherein the composition is suitable for subcutaneous administration.

9. The pharmaceutical composition of claim 6, wherein the composition is suitable for administration as an aerosol.

10. The pharmaceutical composition of claim 2, wherein the composition is in the form of a dosage form.

11. The pharmaceutical composition of claim 10, wherein the dosage form is a tablet or a pill.

12. The pharmaceutical composition of claim 11, wherein the dosage form comprises from 1 to 1000 mg of the compound.

13. A compound selected from the group consisting of:
Compound 505
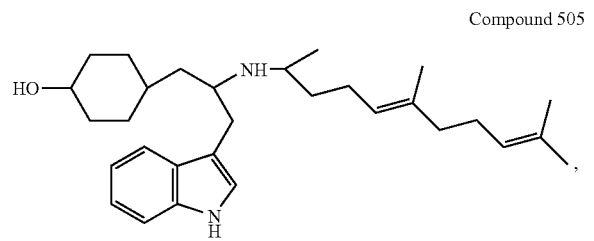
Compound 510
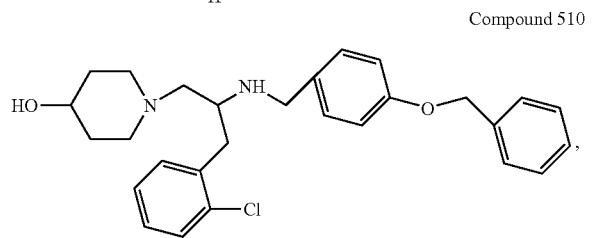
Compound 512
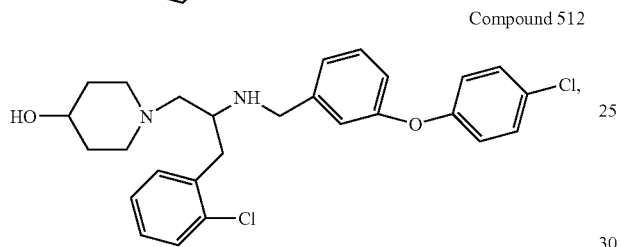
Compound 534
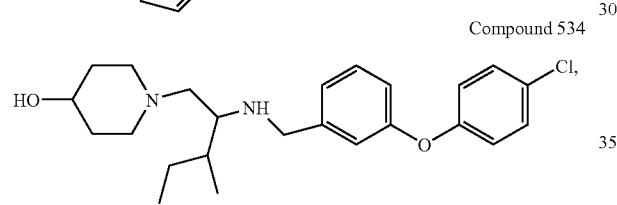
Compound 539
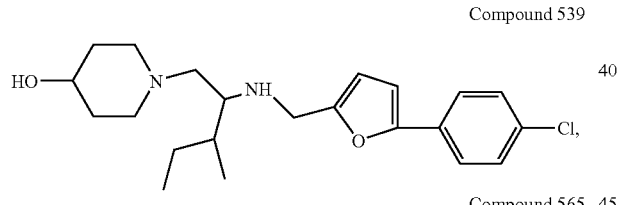
Compound 565
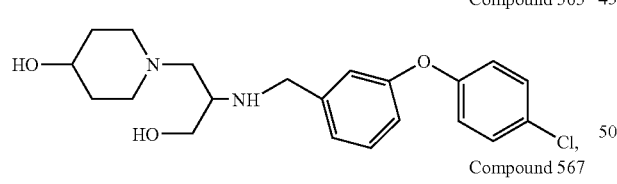
Compound 567
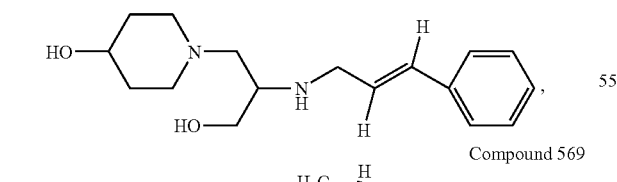
Compound 569
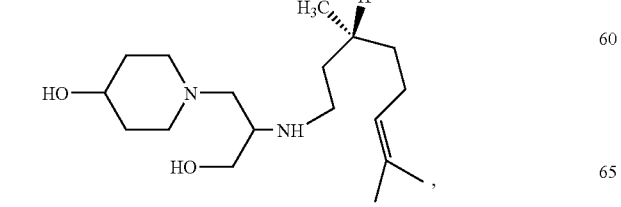
-continued
Compound 576
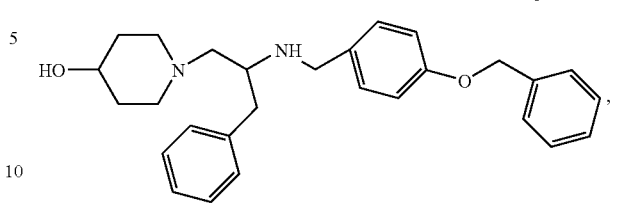
Compound 578
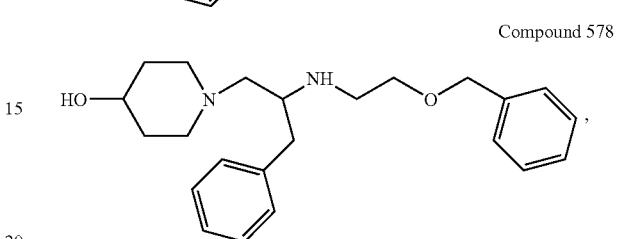
Compound 582
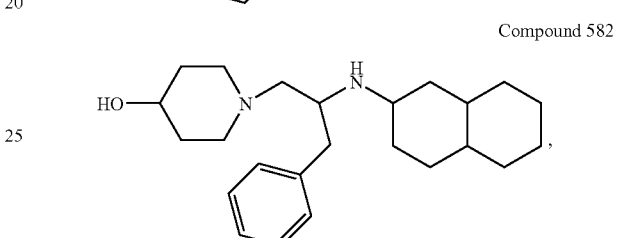
Compound 585
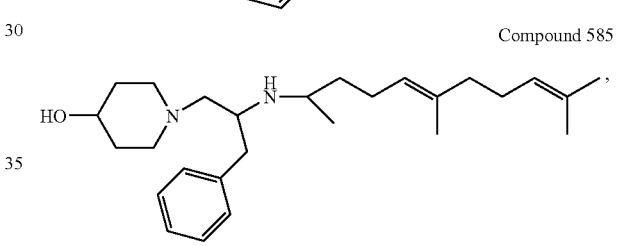
Compound 588
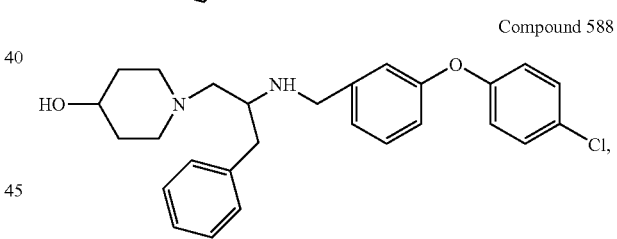
Compound 592
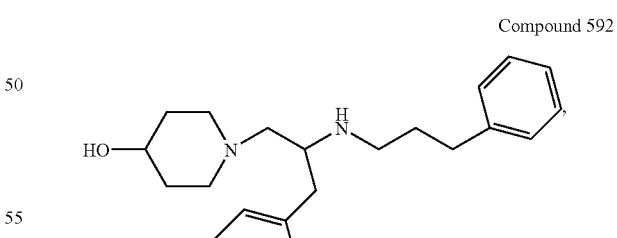
Compound 597
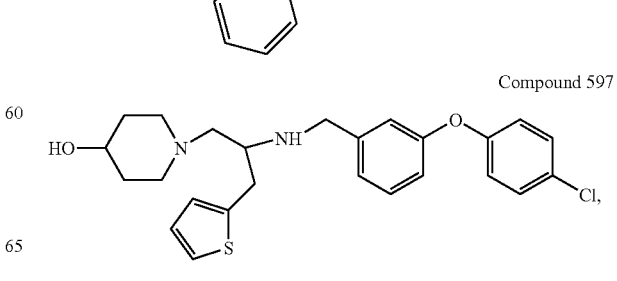

-continued
Compound 602
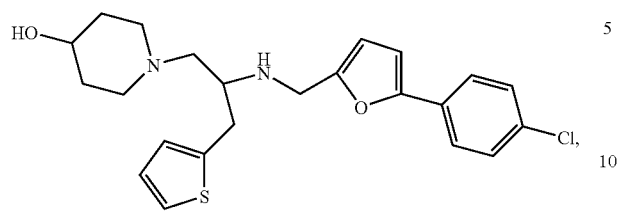
Compound 606
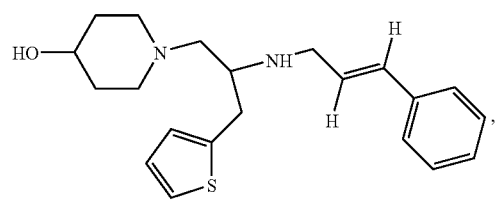
Compound 501
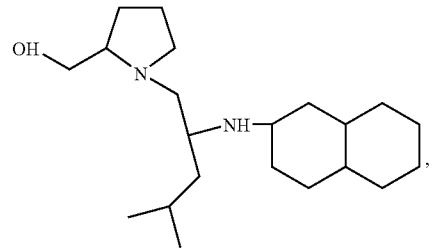
Compound 503
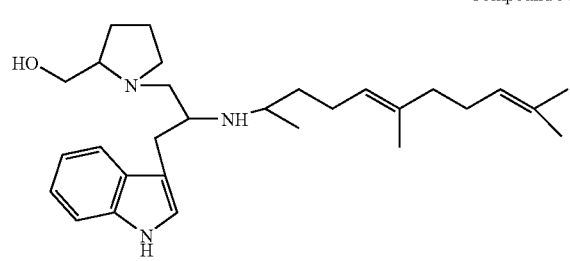
Compound 504
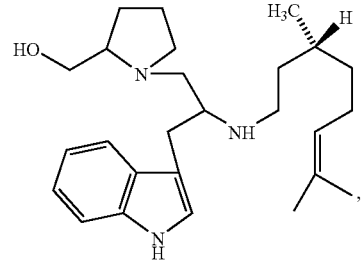
Compound 507
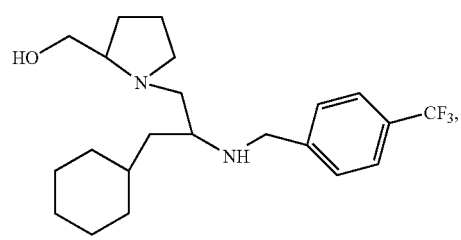
-continued
Compound 508
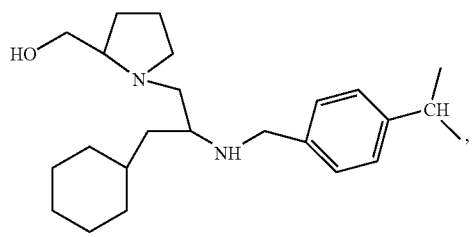
Compound 511
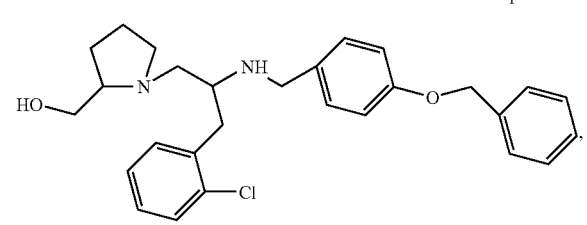
Compound 513
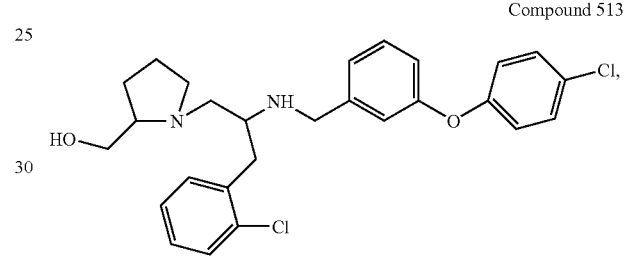
Compound 514
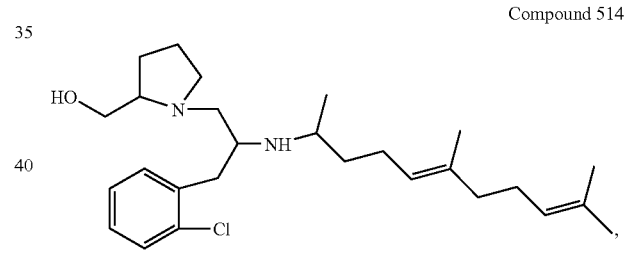
Compound 528
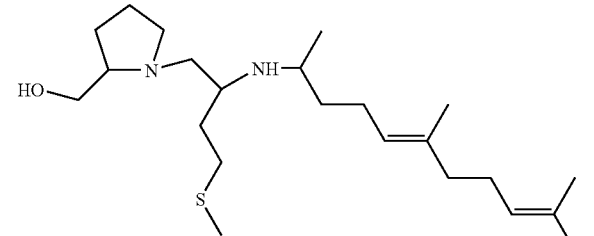
Compound 530
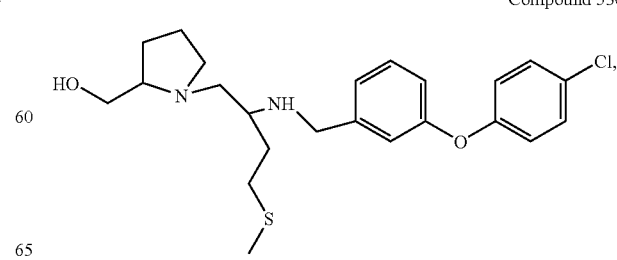

Compound 531
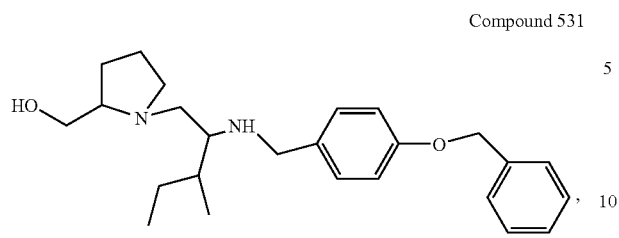
Compound 532
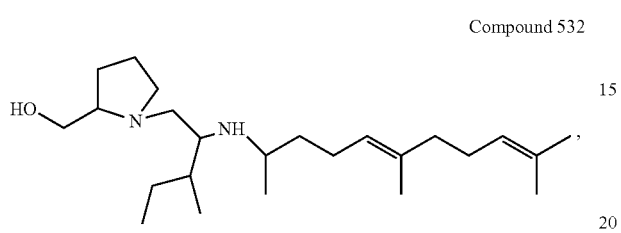
Compound 538
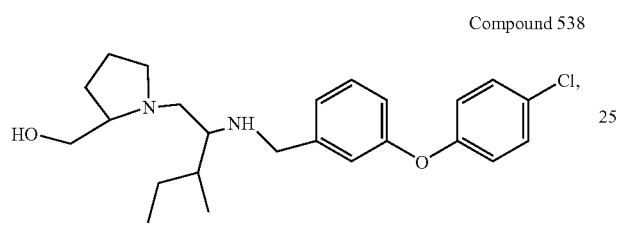
Compound 541
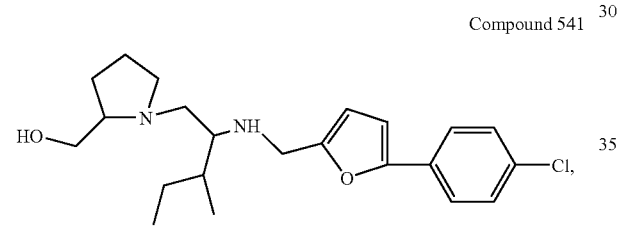
Compound 562
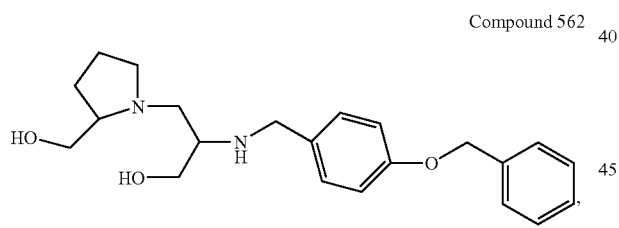
Compound 563
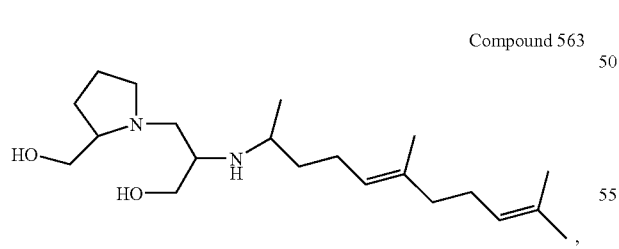
Compound 564
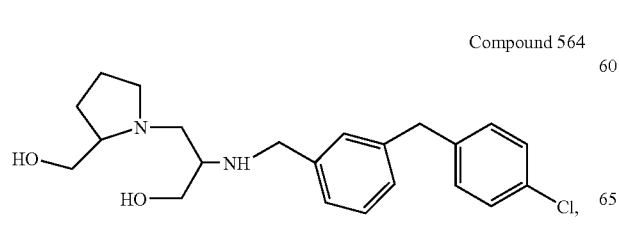
Compound 566
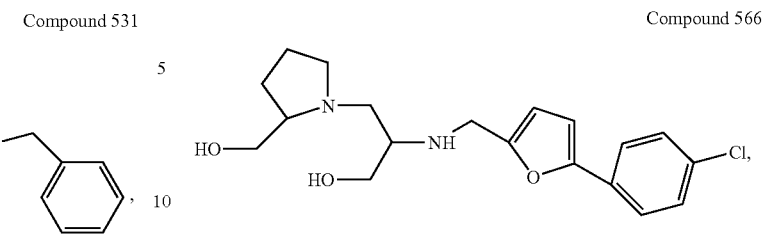
Compound 568
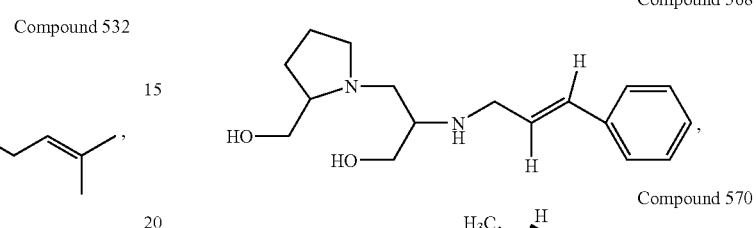
Compound 570
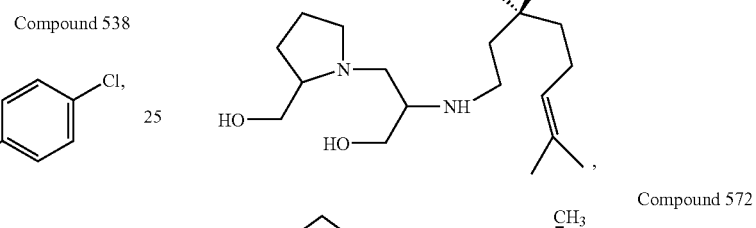
Compound 572
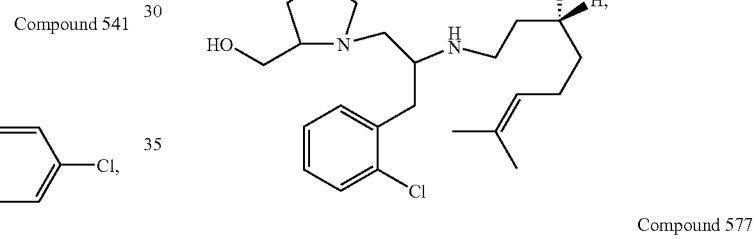
Compound 577
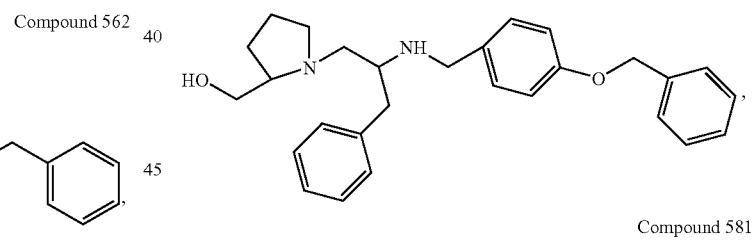
Compound 581
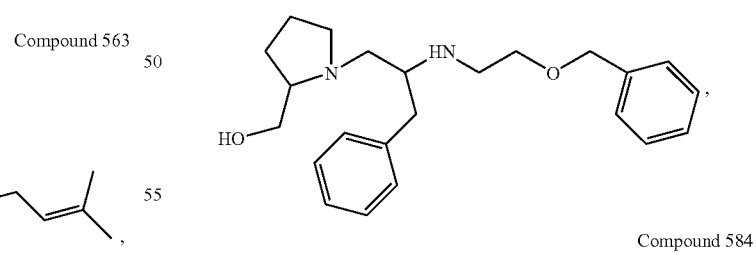
Compound 584
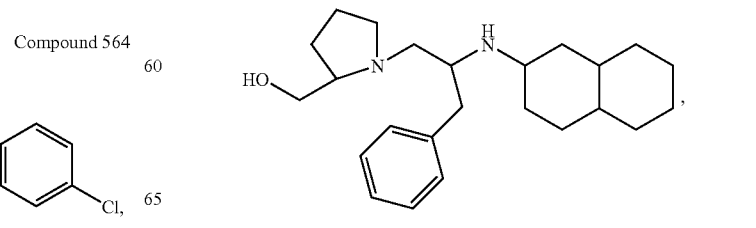

-continued
Compound 587
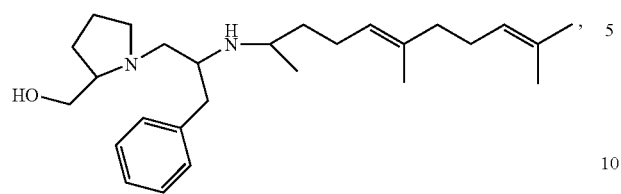
Compound 589
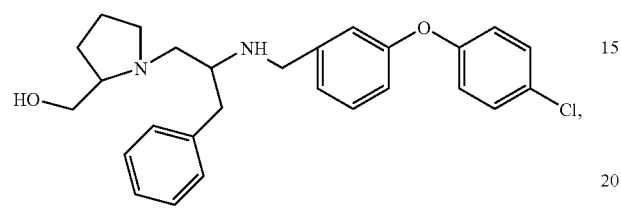
Compound 590
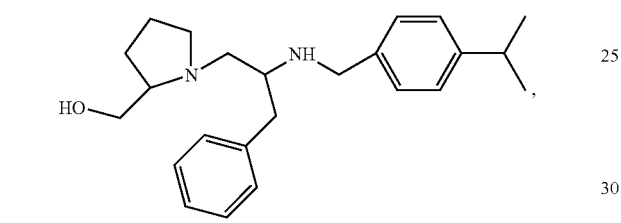
Compound 591
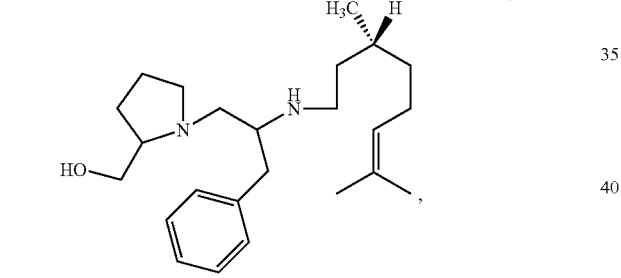
Compound 593
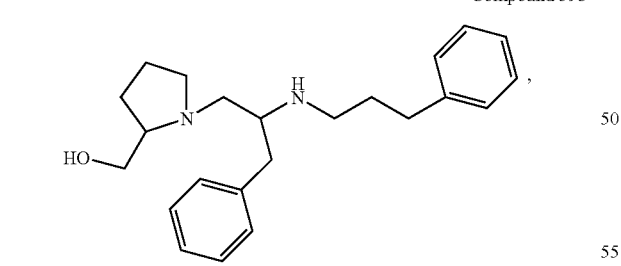
Compound 596
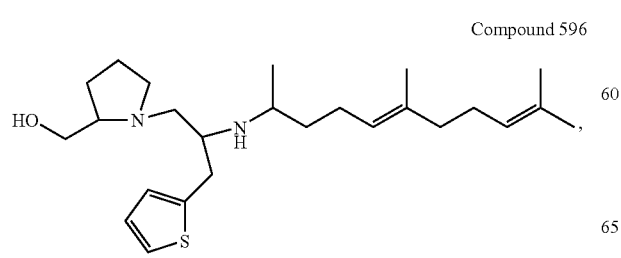
-continued
Compound 600
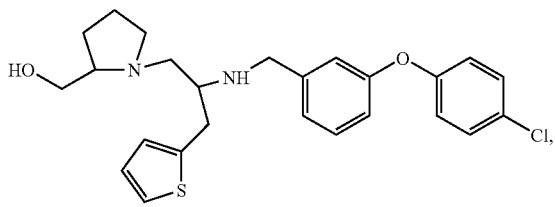
Compound 605
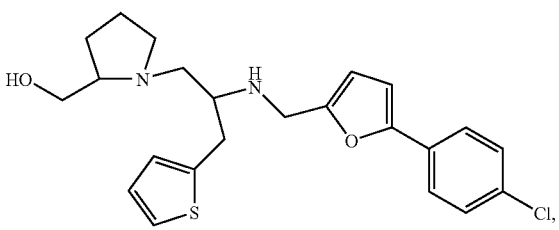
Compound 608
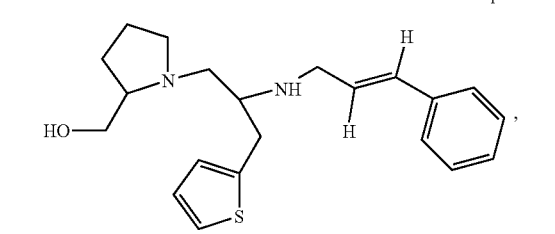
Compound 502
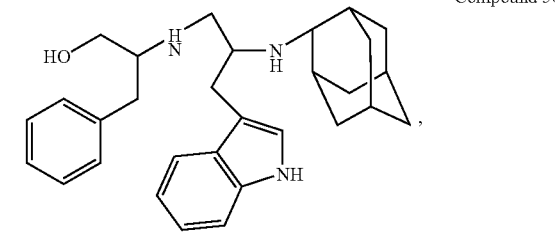
Compound 506
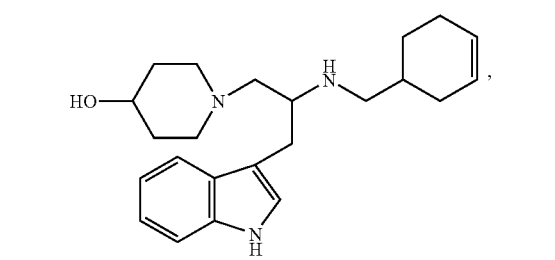
Compound 509
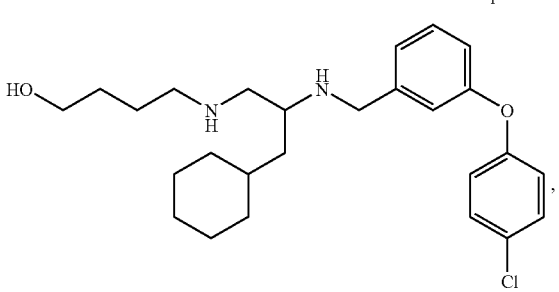

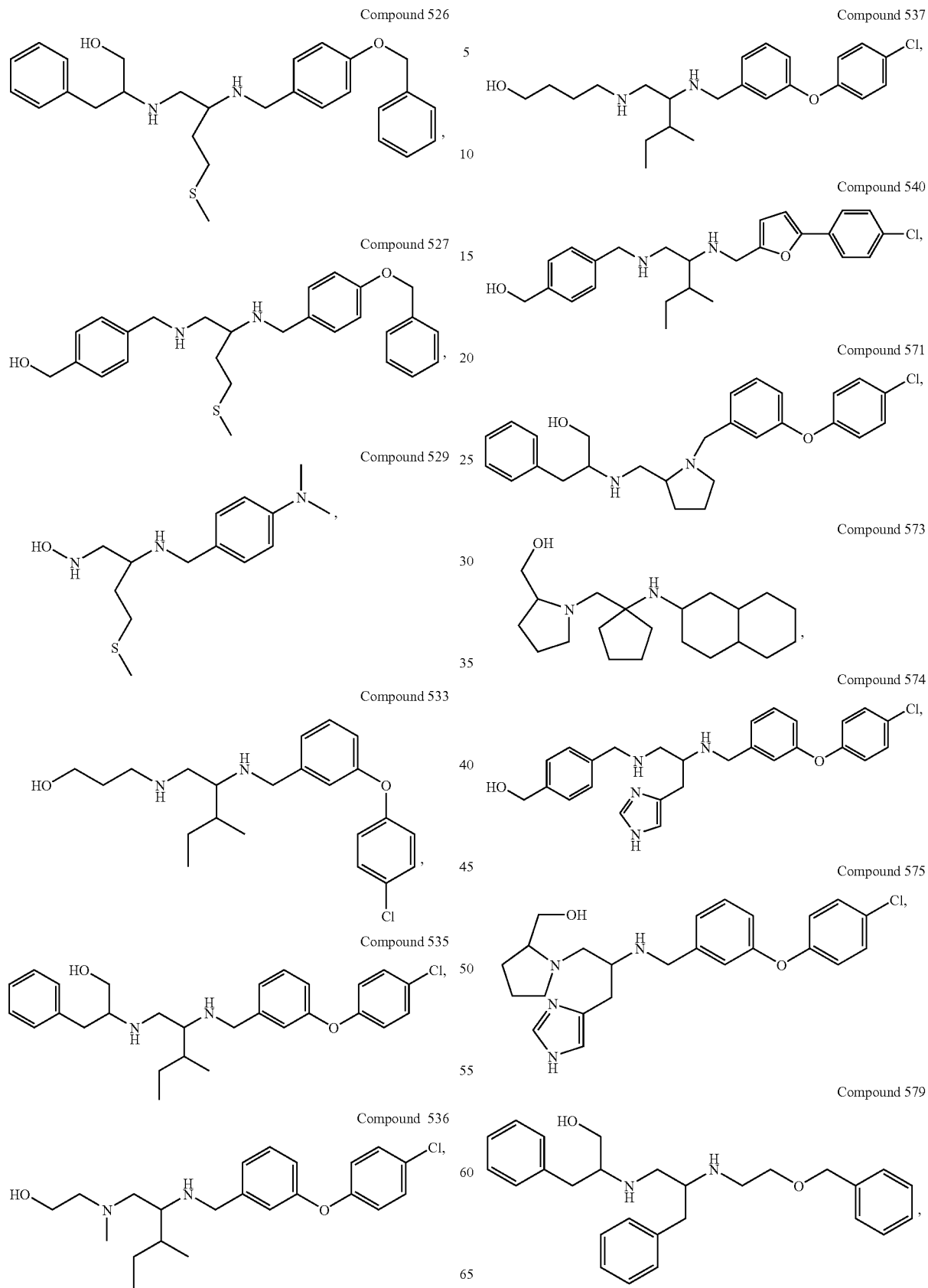

-continued

Compound 580

Compound 583

Compound 586

Compound 594

Compound 595

Compound 598

Compound 599

-continued

Compound 601

Compound 603

Compound 604

Compound 607

, and

Compound 618 or a salt thereof.

14. A pharmaceutical composition comprising a compound of claim 13, and a pharmaceutically acceptable carrier.

15. A compound selected from the group consisting of:

Compound 515

-continued

Compound 516, Compound 517, Compound 518, Compound 518 dbl, Compound 519, Compound 520, Compound 521, Compound 522, Compound 523, Compound 524, Compound 525, Compound 542, Compound 543, Compound 544, Compound 545, Compound 546

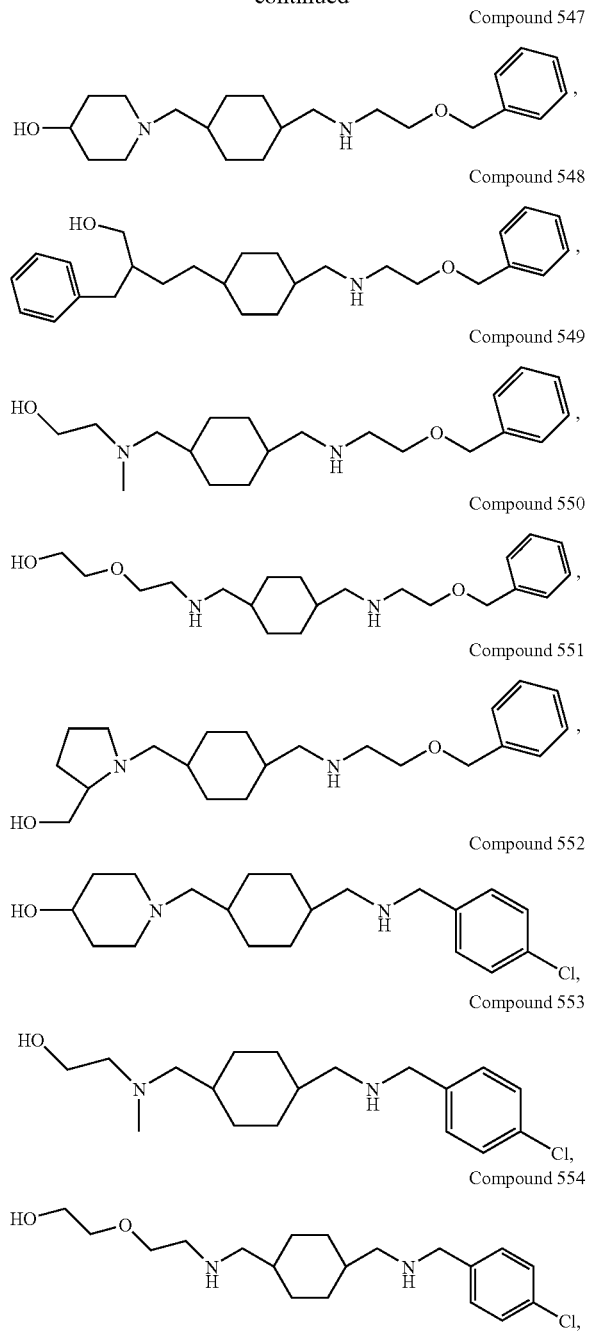
or a salt thereof.
16. A pharmaceutical composition comprising a compound of claim 15, and a pharmaceutically acceptable carrier.

UNITED STATES PATENT AND TRADEMARK OFFICE
CERTIFICATE OF CORRECTION

PATENT NO. : 7,652,039 B2  Page 1 of 1
APPLICATION NO. : 10/441272
DATED : January 26, 2010
INVENTOR(S) : Protopopova et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 728 days.

Signed and Sealed this

Twenty-third Day of November, 2010

David J. Kappos
*Director of the United States Patent and Trademark Office*